(12) United States Patent
Tam et al.

(10) Patent No.: US 9,333,192 B2
(45) Date of Patent: May 10, 2016

(54) PHYTOESTROGEN PRODUCT OF RED CLOVER AND PHARMACEUTICAL USES THEREOF

(71) Applicant: Sinoveda Canada Inc., Edmonton, Alberta (CA)

(72) Inventors: Yun Kau Tam, Edmonton (CA); Yi-Chan James Lin, Edmonton (CA); Brian Duff Sloley, Edmonton (CA); Chih-Yuan Tseng, Edmonton (CA)

(73) Assignee: SINOVEDA CANADA, INC CA (US)

( * ) Notice: Subject to any disclaimer, the term of this patent is extended or adjusted under 35 U.S.C. 154(b) by 0 days.

(21) Appl. No.: 14/242,981

(22) Filed: Apr. 2, 2014

(65) Prior Publication Data
US 2014/0296329 A1    Oct. 2, 2014

Related U.S. Application Data

(63) Continuation-in-part of application No. PCT/IB2012/055277, filed on Oct. 2, 2012, and a continuation-in-part of application No. 14/069,740, filed on Nov. 1, 2013, now abandoned, which is a continuation of application No. 13/251,267, filed on Oct. 2, 2011, now abandoned, which is a continuation-in-part of application No. 13/028,136, filed on Feb. 15, 2011, now abandoned.

(60) Provisional application No. 61/542,253, filed on Oct. 2, 2011, provisional application No. 61/304,589, filed on Feb. 15, 2010.

(51) Int. Cl.
*A61K 31/353* (2006.01)
*A61K 36/48* (2006.01)
*G06F 19/00* (2011.01)

(52) U.S. Cl.
CPC .............. *A61K 31/353* (2013.01); *A61K 36/48* (2013.01); *G06F 19/704* (2013.01)

(58) Field of Classification Search
CPC ..... A61K 31/353; A61K 36/48; G06F 19/704
See application file for complete search history.

(56) References Cited

U.S. PATENT DOCUMENTS

| | | | |
|---|---|---|---|
| 6,060,070 A | 5/2000 | Gorbach | |
| 6,340,703 B1 | 1/2002 | Kelly | |
| 2002/0035074 A1* | 3/2002 | Kelly | 514/27 |
| 2003/0175345 A1 | 9/2003 | Hite et al. | |
| 2009/0028968 A1* | 1/2009 | Tam et al. | 424/757 |
| 2012/0077874 A1 | 3/2012 | Tam et al. | |

FOREIGN PATENT DOCUMENTS

| | | |
|---|---|---|
| CN | 101045045 | 10/2007 |
| CN | 101757640 | 6/2010 |
| WO | 00/64438 | 11/2000 |
| WO | 2008/016768 | 2/2008 |
| WO | 2008/057934 | 5/2008 |
| WO | 2008/120105 | 10/2008 |
| WO | 2013/050930 | 4/2013 |

OTHER PUBLICATIONS

Lee et al, Biol. Pharm. Bull. 28(10) 1948-1953 (2005).*
Moon et al, The AAPS Journal 2006; 8 (3) Article 51.*
U.S. Office Action, May 1, 2013, for U.S. Appl. No. 13/251,267, filed Oct. 2, 2011.
PCT International Search Report, Jan. 25, 2013, for Int' App'l No. PCT/IB2012/055277, filed Oct. 2, 2012.
PCT Written Option, Jan. 25, 2013, for Int' App'l No. PCT/IB2012/055277, filed Oct. 2, 2012.
Abrams, S. A., I. J. Griffin, et al. (2002). "Using stable isotopes to assess the bioavailability of minerals in food fortification programs." Food Nutr Bull 23(3 Suppl): 158-165.
Allred, C. D., K. F. Allred, et al. (2004). "Dietary genistein results in larger MNU-induced, estrogen-dependent mammary tumors following ovariectomy of Sprague-Dawley rats." Carcinogenesis 25(2): 211-218.
Aldenkamp AP, Alpherts WC, Moerland MC, Ottevanger N and Van Parys JA (1987) Controlled releasecarbamazepine: cognitive side effects in patients with epilepsy. Epilepsia 28:507-514.
Atkinson C, Compston JE, Day NE, Dowsett M and Bingham SA (2004) The effects of phytoestrogen isoflavones onbone density in women: a double-blind, randomized, placebo-controlled trial. Am J Clin Nutr 79:326-333.
Baillard, C., A. Bianchi, et al. (2007). "[Anaesthetic preoperative assessment of chronic medications and herbal medicine use: a multicenter survey]." Ann Fr Anesth Reanim 26(2): 132-135.
Beck, V., E. Unterrieder, et al. (2003). "Comparison of hormonal activity (estrogen, androgen and progestin) of standardized plant extracts for large scale use in hormone replacement therapy." J Steroid Biochem Mol Biol 84(2-3): 259-268.
Beck V, Rohr U and Jungbauer A (2005) Phytoestrogens derived from red clover: an alternative to estrogenreplacement therapy? J Steroid Biochem Mol Biol 94:499-518.
Berthois, Y., J. A. Katzenellenbogen, et al. (1986). "Phenol red in tissue culture media is a weak estrogen: implications concerning the study of estrogen-responsive cells in culture." Proc Natl Acad Sci U S A 83(8): 2496-2500.
Booth NL, Overk CR, Yao P, Totura S, Deng Y, Hedayat AA, Bolton JL, Pauli GF and Farnsworth NR (2006a)Seasonal variation of red clover (*Trifolium pratense* L., Fabaceae) isoflavones and estrogenic activity. J Agric FoodChem 54:1277-1282.
Booth NL, Piersen CE, Banuvar S, Geller SE, Shulman LP and Farnsworth NR (2006b) Clinical studies of red clover (*Trifolium pratense*) dietary supplements in menopause: a literature review. Menopause 13:251-264.
Bowey E, Adlercreutz H and Rowland I (2003) Metabolism of isoflavones and lignans by the gut microflora: a study ingerm-free and human flora associated rats. Food Chem Toxicol 41:631-636.
Carrier RL, Miller LA and Ahmed I. (2007) J Control Release. 123(2):78-99.

(Continued)

*Primary Examiner* — Wu-Cheng Winston Shen
*Assistant Examiner* — Jean Cornet
(74) *Attorney, Agent, or Firm* — Law Offices of Albert Wai-Kit Chan, PLLC

(57) ABSTRACT

The present invention provides compositions comprising optimized ratios of Red clover phytoestrogens as determined by a proprietary physiologically based pharmacokinetic and pharmacodynamic model. The compositions are useful for modulating bone remodeling, and prevention and treatment of osteoporosis.

10 Claims, 15 Drawing Sheets

(56) References Cited

OTHER PUBLICATIONS

Cassidy, A., P. Albertazzi, et al. (2006). "Critical review of health effects of soyabean phyto-oestrogens in post-menopausal women." Proc Nutr Soc 65(1): 76-92.
Chang HC, Churchwell MI, Delclos KB, Newbold RR and Doerge DR (2000) Mass spectrometric determination ofGenistein tissue distribution in diet-exposed Sprague-Dawley rats. J Nutr 130:1963-1970.
Chen, X., S. C. Garner, et al. (2003). "Effects of genistein on expression of bone markers during MC3T3-E1 osteoblastic cell differentiation." J Nutr Biochem 14(6): 342-349.
Chen J, Lin H and Hu M (2005a) Absorption and metabolism of genistein and its five isoflavone analogs in the humanintestinal Caco-2 model. Cancer Chemother Pharmacol 55:159-169.
Chen J, Wang S, Jia X, Bajimaya S, Lin H, Tam VH and Hu M (2005b) Disposition of flavonoids via recycling: comparison of intestinal versus hepatic disposition. Drug Metab Dispos 33:1777-1784.
Clifton-Bligh PB, Baber RJ, Fulcher GR, Nery ML and Moreton T (2001) The effect of isoflavones extracted from redclover (Rimostil) on lipid and bone metabolism. Menopause 8:259-265.
Coldham NG and Sauer MJ (2000) Pharmacokinetics of [(14)C]Genistein in the rat: gender-related differences, potential mechanisms of biological action, and implications for human health. Toxicol Appl Pharmacol 164:206-215.
Daruházi AE, Szente L, Balogh B, Matyus P, Beni S, Takacs M, Gergely A, Horvath P, Szoke E and Lemberkovics E. (2008) J Pharm Biomed Anal. 4;48(3):636-40.
Day AJ, DuPont MS, Ridley S, Rhodes M, Rhodes MJ, Morgan MR and Williamson G (1998) Deglycosylation offlavonoid and isoflavonoid glycosides by human small intestine and liver beta-glucosidase activity. FEBS Lett436:71-75.
Dong, T. T., K. J. Zhao, et al. (2006). "Chemical and biological assessment of a chinese herbal decoction containing Radix Astragali and Radix Angelicae Sinensis: Determination of drug ratio in having optimized properties." J Agric Food Chem 54(7): 2767-2774.
Engelhardt PF and Riedl CR (2008a) Effects of one-year treatment with isoflavone extract from red clover on prostate, liver function, sexual function, and quality of life in men with elevated PSA levels and negative prostate biopsy findings. Urology 71:185-190; discussion 190.
Engelhardt PF and Riedl CR (2008b) Reply to editorial comment, Re: Engelhardt PF and Riedl CR, Effects of one-yeartreatment with isoflavone extract from red clover on prostate, liver function, sexual function, and quality of life in menwith elevated PSA levels and negative prostate biopsy findings. Urology 71: 190, 2008. Urology 71:987.
Eriksen, E. F. (2010). "Cellular mechanisms of bone remodeling." Rev Endocr Metab Disord 11(4): 219-227.
Fernandez E, Gallus S, Bosetti C, Franceschi S, Negri E and La Vecchia C (2003) Hormone replacement therapy andcancer risk: a systematic analysis from a network of case-control studies. Int J Cancer 105:408-412.
Former, P., C. Theurer, et al. (2006). "Visualization and analysis of the release mechanism of shellac coated ascorbic acid pellets." Pharmazie 61(12): 1005-1008.
Frishman WH and Lazar EJ (1992) Sustained-release verapamil formulations for treating hypertension. J ClinPharmacol 32:455-462.
Fujita, T. and M. Fukase (1992). "Comparison of osteoporosis and calcium intake between Japan and the United States." Proc Soc Exp Biol Med 200(2): 149-152. (Abstract).
Gambacciani M, Ciaponi M and Genazzani AR (2007) The HRT misuse and osteoporosis epidemic: a possible futurescenario. Climacteric 10:273-275.
Gambacciani M, Monteleone P, Sacco A and Genazzani AR (2003) Hormone replacement therapy and endometrial, ovarian and colorectal cancer. Best Pract Res Clin Endocrinol Metab 17:139-147.
Garcia Palacios, V., L. J. Robinson, et al. (2005). "Negative regulation of RANKL-induced osteoclastic differentiation in RAW264.7 Cells by estrogen and phytoestrogens." J Biol Chem 280(14): 13720-13727.

Ge Y, Chen D, Xie L and zhang R (2006) Enhancing effect of daidzein on the differentiation and mineralization inmouse osteoblast-like MC3T3-E1 cells. Yakugaku Zasshi 126:651-656.
Gu L, Laly M, Chang HC, Prior RL, Fang N, Ronis MJ and Badger TM (2005) Isoflavone conjugates areunderestimated in tissues using enzymatic hydrolysis. J Agric Food Chem 53:6858-6863.
Hale, G. E., C. L. Hughes, et al. (2001). "A double-blind randomized study on the effects of red clover isoflavones on the endometrium." Menopause 8(5): 338-346.
Han LM, Guo J, Zhang LJ, Wang QS and Fang XL (2006) Pharmacokinetics and biodistribution of polymeric micellesof paclitaxel with Pluronic P123. Acta Pharmacol Sin 27:747-753.
Heinonen SM, Wahala K and Adlercreutz H (2004) Identification of urinary metabolites of the red clover isoflavonesformononetin and biochanin A in human subjects. J Agric Food Chem 52:6802-6809.
Hirsh J, Bauer KA, Donati MB, Gould M, Samama MM, Weitz JI and American College of Chest Physicians (2008) Parenteral anticoagulants: American College of Chest Physicians Evidence-Based Clinical Practice Guidelines (8th Edition). Chest. 133(6 Suppl):141S-159S.
Howes J, Waring M, Huang L and Howes LG (2002) Long-term pharmacokinetics of an extract of isoflavones from redclover (*Trifolium pratense*). J Altern Complement Med 8:135-142.
Hur, H. and F. Rafii (2000). "Biotransformation of the isoflavonoids biochanin A, formononetin, and glycitein by Eubacterium limosum." FEMS Microbiol Lett 192(1): 21-25.
Izumi T, Piskula MK, Osawa S, Obata A, Tobe K, Saito M, Kataoka S, Kubota Y and Kikuchi M (2000) Soy isoflavoneaglycones are absorbed faster and in higher amounts than their glucosides in humans. J Nutr 130:1695-1699.
Ji, Z. N., W. Y. Zhao, et al. (2006). "In vitro estrogenic activity of formononetin by two bioassay systems." Gynecol Endocrinol 22(10): 578-584.
Jia X, Chen J, Lin H and Hu M (2004) Disposition of flavonoids via enteric recycling: enzyme-transporter couplingaffects metabolism of biochanin A and formononetin and excretion of their phase II conjugates. J Pharmacol Exp Ther310:1103-1113.
Joseph TB, Wang SW, Liu X, Kulkarni KH, Wang J, Xu H and Hu M (2007) Disposition of flavonoids via entericrecycling: enzyme stability affects characterization of prunetin glucuronidation across species, organs, and UGTisoforms. Mol Pharm 4:883-894.
Kano M, Takayanagi T, Harada K, Sawada S and Ishikawa F (2006) Bioavailability of isoflavones after ingestion of soybeverages in healthy adults. J Nutr 136:2291-2296.
Krenn, L., I. Unterrieder and R. Ruprechter (2002). Quantification of isoflavones in red clover by high-performance liquid chromatography. J Chromatogr B Analyt Technol Biomed Life Sci 777(1-2): 123-128.
Kuiper GG, Carlsson B, Grandien K, Enmark E, Haggblad J, Nilsson S and Gustafsson JA (1997) Comparison of theligand binding specificity and transcript tissue distribution of estrogen receptors alpha and beta. Endocrinology138:863-870.
Lagari, V. S. and S. Levis (2014). Phytoestrogens for menopausal bone loss and climacteric symptoms. J Steroid Biochem Mol Biol 139: 294-301.
Laza-Knoerr AL, Gref R and Couvreur P. (2010) Cyclodextrins for drug delivery. J Drug Target. 18(9):645-56.
Lee SH, Kim YH, Yu HJ, Cho NS, Kim TH, Kim DC, Chung CB, Hwang YI and Kim KH. (2007) Biosci Biotechnol Biochem. 71(12):2927-33.
Lee, K. H. and E. M. Choi (2005). "Biochanin a Stimulates Osteoblastic Differentiation and Inhibits Hydrogen Peroxide-Induced Production of Inflammatory Mediators in MC3T3-E1 Cells." Biol. Pharm. Bull. 28(10): 1948-1953.
Li XH, Zhang JC, Sui SF and Yang MS (2005) Effect of daidzin, genistin, and glycitin on osteogenic and adipogenicdifferentiation of bone marrow stromal cells and adipocytic transdifferentiation of osteoblasts. Acta Pharmacol Sin26:1081-1086.
Li S, Wang A, Jiang W and Guan Z (2008) Pharmacokinetic characteristics and anticancer effects of 5-fluorouracilloaded nanoparticles. BMC Cancer 8:103.
Liu J, Burdette JE, Xu H, Gu C, van Breemen RB, Bhat KP, Booth N, Constantinou AI, Pezzuto JM, Fong HH, Farnsworth NR and Bolton

(56) References Cited

OTHER PUBLICATIONS

JL (2001) Evaluation of estrogenic activity of plant extracts for the potential treatment ofmenopausal symptoms. J Agric Food Chem 49:2472-2479.

Liu Y and Hu M (2002) Absorption and metabolism of flavonoids in the caco-2 cell culture model and a perused ratintestinal model. Drug Metab Dispos 30:370-377.

Ma DF, Qin LQ, Wang PY and Katoh R (2008) Soy isoflavone intake inhibits bone resorption and stimulates boneformation in menopausal women: meta-analysis of randomized controlled trials. Eur J Clin Nutr 62:155-161.

Magee, P. J. (2011). Is equol production beneficial to health? Proc Nutr Soc 70(1): 10-18.

Mahmud A, Xiong XB and Lavasanifar A (2008) Development of novel polymeric micellar drug conjugates and nanocontainerswith hydrolyzable core structure for doxorubicin delivery. Eur J Pharm Biopharm.

Mathey, J., V. Lamothe, et al. (2006). "Concentrations of isoflavones in plasma and urine of post-menopausal women chronically ingesting high quantities of soy isoflavones." J Pharm Biomed Anal 41(3): 957-965.

Mitrovic V, Gessner C, Hain P, Muller KD and Schlepper M (1991) Hemodynamic, anti-ischemic, and neurohumoraleffects of slow-release isosorbide-5-mononitrate in patients with coronary artery disease after short- and long-termtherapy. Clin Cardiol 14:209-218.

Moon YJ, Sagawa K, Frederick K, Zhang S and Morris ME (2006) Pharmacokinetics and bioavailability of theisoflavone biochanin A in rats. Aaps J 8:E433-442.

Nagel SC, vom Saal FS and Welshons WV (1998) The effective free fraction of estradiol and xenoestrogens in humanserum measured by whole cell uptake assays: physiology of delivery modifies estrogenic activity. Proc Soc Exp BiolMed 217:300-309.

Nelson, H. D., K. K. Vesco, et al. (2006). "Nonhormonal therapies for menopausal hot flashes: systematic review and meta-analysis." Jama 295(17): 2057-2071.

Overk CR, Yao P, Chadwick LR, Nikolic D, Sun Y, Cuendet MA, Deng Y, Hedayat AS, Pauli GF, Farnsworth NR, vanBreemen RB and Bolton JL (2005) Comparison of the in vitro estrogenic activities of compounds from hops (Humuluslupulus) and red clover (*Trifolium pratense*). J Agric Food Chem 53:6246-6253.

Pearnchob, N. and R. Bodmeier (2003a). "Dry polymer powder coating and comparison with conventional liquid-based coatings for Eudragit) RS, ethylcellulose and shellac." Eur J Pharm Biopharm 56(3): 363-369.

Pearnchob, N., A. Dashevsky, et al. (2004). "Improvement in the disintegration of shellac-coated soft gelatin capsules in simulated intestinal fluid." J Control Release 94(2-3): 313-321.

Pearnchob, N., J. Siepmann, et al. (2003b). "Pharmaceutical applications of shellac: moisture-protective and taste-masking coatings and extended-release matrix tablets." Drug Dev Ind Pharm 29(8): 925-938.

Pike AC, Brzozowski AM, Hubbard RE, Bonn T, Thorsell AG, Engstrom O, Ljunggren J, Gustafsson JA and CarlquistM (1999) Structure of the ligand-binding domain of oestrogen receptor beta in the presence of a partial agonist and afull antagonist. Embo J 18:4608-4618.

Rachon D, Menche A, Vortherms T, Seidlova-Wuttke D and Wuttke W (2008) Effects of dietary equol administration onthe mammary gland in ovariectomized Sprague-Dawley rats. Menopause 15:340-345.

Rachon D, Vortherms T, Seidlova-Wuttke D, Menche A and Wuttke W (2007) Uterotropic effects of dietary equoladministration in ovariectomized Sprague-Dawley rats. Climacteric 10:416-426.

Richelle M, Pridmore-Merten S, Bodenstab S, Enslen M and Offord EA (2002) Hydrolysis of isoflavone glycosides toaglycones by beta-glycosidase does not alter plasma and urine isoflavone pharmacokinetics in postmenopausalwomen. J Nutr 132:2587-2592.

Rimoldi G, Christoffel J, Seidlova-Wuttke D, Jarry H and Wuttke W (2007) Effects of chronic genistein treatment inmammary gland, uterus, and vagina. Environ Health Perspect 115 Suppl 1:62-68.

Rufer CE, Maul R, Donauer E, Fabian EJ and Kulling SE (2007) In vitro and in vivo metabolism of the soy isoflavoneglycitein. Mol Nutr Food Res 51:813-823.

Schneider, H., R. Simmering, et al. (2000). "Degradation of quercetin-3-glucoside in gnotobiotic rats associated with human intestinal bacteria." J Appl Microbiol 89(6): 1027-1037.

Schult TM, Ensrud KE, Blackwell T, Ettinger B, Wallace R and Tice JA (2004) Effect of isoflavones on lipids and boneturnover markers in menopausal women. Maturitas 48:209-218.

Seelig MS, Altura BM and Altura BT (2004) Benefits and risks of sex hormone replacement in postmenopausalwomen. J Am Coll Nutr 23:482S-496S.

Sepehr E, Cooke G, Robertson P and Gilani GS (2007) Bioavailability of soy isoflavones in rats Part I: application ofaccurate methodology for studying the effects of gender and source of isoflavones. Mol Nutr Food Res 51:799-812.

Setchell KD, Brown NM, Desai P, Zimmer-Nechemias L, Wolfe BE, Brashear WT, Kirschner AA, Cassidy A and HeubiJE (2001) Bioavailability of pure isoflavones in healthy humans and analysis of commercial soy isoflavonesupplements. J Nutr 131:1362S-1375S.

Setchell KD, Brown NM, Desai PB, Zimmer-Nechimias L, Wolfe B, Jakate AS, Creutzinger V and Heubi JE (2003a) Bioavailability, disposition, and dose-response effects of soy isoflavones when consumed by healthy women atphysiologically typical dietary intakes. J Nutr 133:1027-1035.

Setchell KD, Brown NM, Zimmer-Nechemias L, Brashear WT, Wolfe BE, Kirschner AA and Heubi JE (2002) Evidencefor lack of absorption of soy isoflavone glycosides in humans, supporting the crucial role of intestinal metabolism forbioavailability. Am J Clin Nutr 76:447-453.

Setchell KD and Cassidy A (1999) Dietary isoflavones: biological effects and relevance to human health. J Nutr129:758S-767S.

Setchell KD, Clerici C, Lephart ED, Cole SJ, Heenan C, Castellani D, Wolfe BE, Nechemias-Zimmer L, Brown NM, Lund TD, Handa RJ and Heubi JE (2005) S-equol, a potent ligand for estrogen receptor beta, is the exclusiveenantiomeric form of the soy isoflavone metabolite produced by human intestinal bacterial flora. Am J Clin Nutr81:1072-1079.

Setchell KD and Cole SJ (2006) Method of defining equol-producer status and its frequency among vegetarians. J Nutr136:2188-2193.

Setchell KD, Faughnan MS, Avades T, Zimmer-Nechemias L, Brown NM, Wolfe BE, Brashear WT, Desai P, OldfieldMF, Botting NP and Cassidy A (2003b) Comparing the pharmacokinetics of daidzein and genistein with the use of13C-labeled tracers in premenopausal women. Am J Clin Nutr 77:411-419.

Setchell KD and Lydeking-Olsen E (2003) Dietary phytoestrogens and their effect on bone: evidence from in vitro andin vivo, human observational, and dietary intervention studies. Am J Clin Nutr 78(suppl):593S-609S.

Sugimoto, E. and M. Yamaguchi (2000a). "Anabolic effect of genistein in osteoblastic MC3T3-E1 cells." Int J Mol Med 5(5): 515-520. (Abstract).

Sugimoto, E. and M. Yamaguchi (2000b). "Stimulatory effect of Daidzein in osteoblastic MC3T3-E1 cells." Biochem Pharmacol 59(5): 471-475.

Thompson Lu, Boucher BA, Cotterchio M, Kreiger N and Liu Z (2007) Dietary phytoestrogens, including isoflavones, lignans, and coumestrol, in nonvitamin, nonmineral supplements commonly consumed by women in Canada. NutrCancer 59:176-184.

Tobe, H., O. Komiyama, et al. (1997). "Daidzein stimulation of bone resorption in pit formation assay." Biosci Biotechnol Biochem 61(2): 370-371.

Tolleson, W. H., D. R. Doerge, et al. (2002). "Metabolism of biochanin A and formononetin by human liver microsomes in vitro." J Agric Food Chem 50(17): 4783-4790.

Tsao, R., Y. Papadopoulos, R. Yang, J. C. Young and K. McRae (2006). Isoflavone profiles of red clovers and their distribution in different parts harvested at different growing stages. J. Agric. Food Chem. 54: 5797-5805.

Tseng, C.-Y. (2006). "Entropic criterion for model selection." Physica A 370(2): 530-538.

Tsunoda N, Pomeroy S and Nestel P (2002) Absorption in humans of isoflavones from soy and red clover is similar. JNutr 132:2199-2201.

(56) References Cited

OTHER PUBLICATIONS

Wang, S. W., J. Chen, et al. (2006). "Disposition of flavonoids via enteric recycling: structural effects and lack of correlations between in vitro and in situ metabolic properties." Drug Metab Dispos 34(11): 1837-1848.

Wang SW, Chen Y, Joseph T and Hu M (2008) Variable isoflavone content of red clover products affects intestinaldisposition of biochanin A, formononetin, genistein, and daidzein. J Altern Complement Med 14:287-297.

Wende, K., L. Krenn, et al. (2004). "Red clover extracts stimulate differentiation of human osteoblastic osteosarcoma HOS58 cells." Planta Med 70(10): 1003-1005.

Wuttke W, Jarry H and Seidlova-Wuttke D (2007) Isoflavones—safe food additives or dangerous drugs? Ageing ResRev 6:150-188.

Yan R, Ko NL, Li SL, Tam YK and Lin G. (2008) Pharmacokinetics and metabolism of ligustilide, a major bioactive component in Rhizoma Chuanxiong, in the rat. Drug Metab Dispos. 36(2):400-8.

Yoshida K, Tsukamoto T, Torii H, Doi T, Naeshiro I, Shibata K, Uemura I and Tanayama S (1985) Disposition ofipriflavone (TC-80) in rats and dogs. Radioisotopes 34:618-623.

Zentner GM, Rathi R, Shih C, McRea JC, Seo MH, Oh H, Rhee BG, Mestecky J, Moldoveanu Z, Morgan M andWeitman S (2001) Biodegradable block copolymers for delivery of proteins and water-insoluble drugs. J Control Release 72:203-215.

Zubik L and Meydani M (2003) Bioavailability of soybean isoflavones from aglycone and glucoside forms in Americanwomen. Am J Clin Nutr 77:1459-1465.

\* cited by examiner

PHYTOESTROGEN PRODUCT OF RED CLOVER AND PHARMACEUTICAL USES THEREOF

This application is a continuation-in-part application of International Application No. PCT/IB2012/055277, filed Oct. 2, 2012, which claims benefit of U.S. App'l Ser. No. 61/542,253, filed Oct. 2, 2011; this application also is a continuation-in-part application of U.S. application Ser. No. 14/069,740, filed Nov. 1, 2013, which is a continuation of U.S. application Ser. No. 13/251,267, filed Oct. 2, 2011, which is a continuation-in-part of U.S. application Ser. No. 13/028,136, filed Feb. 15, 2011, which claims benefit of U.S. App'l Ser. No. 61/304,589, filed Feb. 15, 2010, the contents of which are incorporated herein by reference in its entirety.

BACKGROUND OF THE INVENTION

Deficiency of estrogens during menopause can lead to a number of complications including hot flushes, reduced bone density, mood swings, etc. These symptoms are commonly treated with synthetic hormones. Although the rate of bone density reduction can be alleviated, hormone replacement therapy (HRT) was discovered to be associated with increased cardiovascular disorders in one of the largest studies of its kind (Women's health Initiative, WHI) (Seelig, Altura et al. 2004). HRT was also linked to increased risk of breast and ovarian cancer (Fernandez, Gallus et al. 2003, Gambacciani, Monteleone et al. 2003). After the WHI trial results were published, the use of HRT was reduced dramatically. Many postmenopausal women have resorted to alternative therapy because phytoestrogens are generally considered to be safe and efficacious. The use of soy and Red clover (*Trifolium pratense*), which are rich in phytoestrogens, has been on the rise (Beck, Rohr et al. 2005). Despite the trend, clinical trial results on phytoestrogens, however, have been equivocal (Beck, Rohr et al. 2005, Booth, Piersen et al. 2006, Wuttke, Jarry et al. 2007, Ma, Qin et al. 2008). Alternative therapy has not replaced HRT effectively. A recent study showed that the trend of women moving away from HRT has led to an alarming increase in bone fractures and it is estimated that fractures related to menopause is expected to exceed 40,000 per year in women aged 65-69 years (Gambacciani, Ciaponi et al. 2007). Since the side effects of HRT were publicized after the WHI trial, it has since been reevaluated. There is no consensus with regard to HRT's safety among the medical research community. Therefore, a much closer look at the 'less than expected' effects of phytoestrogens should be undertaken because the toxicity profile of this type of products is so much more favorable.

The major bioactive isoflavones in soy are genistein, daidzein, glycitein and prunetin (Setchell and Cassidy 1999). They are also present in their glycoside forms. There are three classes of bioactives in red clover: isoflavones, coumestrols and lignans (Beck, Rohr et al. 2005). The quantity of coumestrols and lignans is small; therefore, their contribution to the overall activity is likely minimal. The major isoflavones in red clover are Biochanin A and Formononetin (Liu, Burdette et al. 2001, Overk, Yao et al. 2005, Booth, Overk et al. 2006). Genistein and daidzein are present in minute quantities. Biochanin A and Formononetin are precursors of their respective active moieties, genistein and daidzein. The conversion takes place in the intestine by intestinal flora and liver, although the relative significance has not been established. Daidzein is converted by bacteria in the colon to form a more estrogenic metabolite, equol. In Red clover, a significant quantity of Biochanin A and Formononetin is in the form of glycosides. The glycosides in soy and red clover are converted to their respective aglycones by the intestinal flora before absorption (Setchell and Cassidy 1999).

Relative absorption of isoflavone glycoside and their respective aglycones is a subject of controversy. Although the cause of controversy is not readily apparent, the low solubility of the aglycones in a preparation may have a profound effect on their dissolution, metabolism and absorption.

Formononetin and Biochanin A are de-methylated by the intestinal micro flora to produce two active metabolites daidzein and genistein, respectively (Hur and Rafii 2000). However, the site of this metabolic pathway is questioned (Tolleson, Doerge et al. 2002).

Metabolism of isoflavones is mainly mediated by Phase II enzymes in the enterocytes and hepatocytes. Although metabolism of individual isoflavones in rats has been well characterized (Jia, Chen et al. 2004, Chen, Lin et al. 2005, Chen, Wang et al. 2005), interaction between components has not been evaluated.

Clinical studies show that extracts of red clover or soy are safe; however, their efficacies are also equivocal (Booth, Piersen et al. 2006). Although there are proprietary products in the market, which have shown potentials for treating or preventing postmenopausal osteoporosis, these products unfortunately, do not have the quality of a drug. The major shortcomings for the design of these products in the market are that they have not taken into consideration of the interplay between pharmacokinetics and pharmacodynamics. In other words, proper dosage and/or dosing interval are empirically decided.

In this invention, the interplay between these "active" components is evaluated and quantified using a proprietary physiologically based pharmacokinetic and pharmacodynamic model (PBPKPD).

The dosages of the new products are a small fraction of those available in the market. The advantage of these products is their consistency. By modifying the mode of delivery, the other advantage of this product is the increase in the bioavailability of the aglycones and eliminates the conversion to their respective bioactive metabolites in the colon, which leads to variability in efficacy.

SUMMARY OF THE INVENTION

The present invention discloses a composition of active ingredients in Red clover, which are optimized to reduce the rate of bone loss in postmenopausal women by enhancing bone remodeling. In one embodiment, the composition comprises at least 80% of Biochanin A, and no more than 20% of genistein. In another embodiment, the composition comprises at least 80% of Biochanin A, and at least 2% of genistein. In another embodiment, the composition further comprises Formononetin, daidzein, or a combination of Formononetin and daidzein. In another embodiment, the composition is formulated as a parenteral, buccal, sublingual, and other non-oral dosage forms including, but not limited to, topical, subcutaneous, intramuscular and intravenous dosage forms.

DETAILED DESCRIPTION OF THE FIGURES

Figure 5:
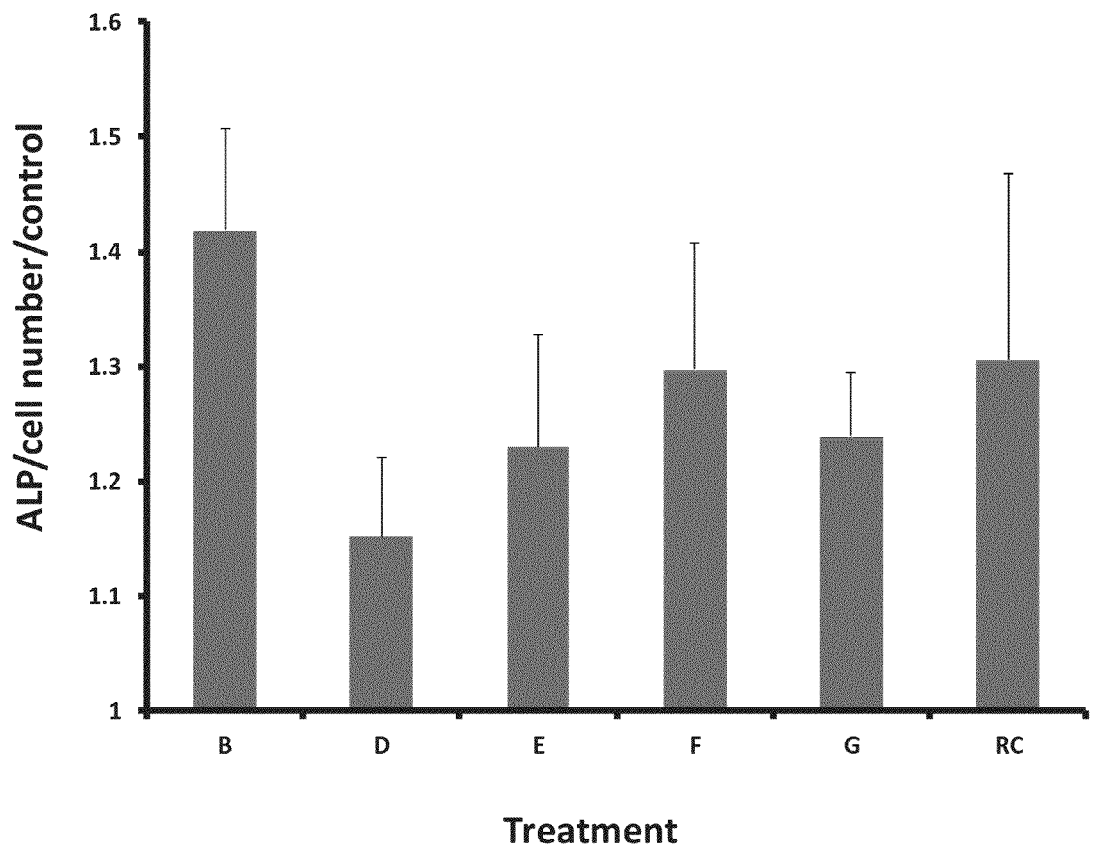

FIG. 5 shows the effects of individual Red clover isoflavones on osteoblast differentiation of MC3T3 cells. The total concentration of isoflavone in each treatment is 10 μM. B: Biochanin A; D: daidzein; E: equol; F: formononetin; G: genistein; and RC: Red clover extract. ALP/cell number ratio obtained in each treatment is normalized by the control to quantify relative osteoblast activities.

Figure 6:
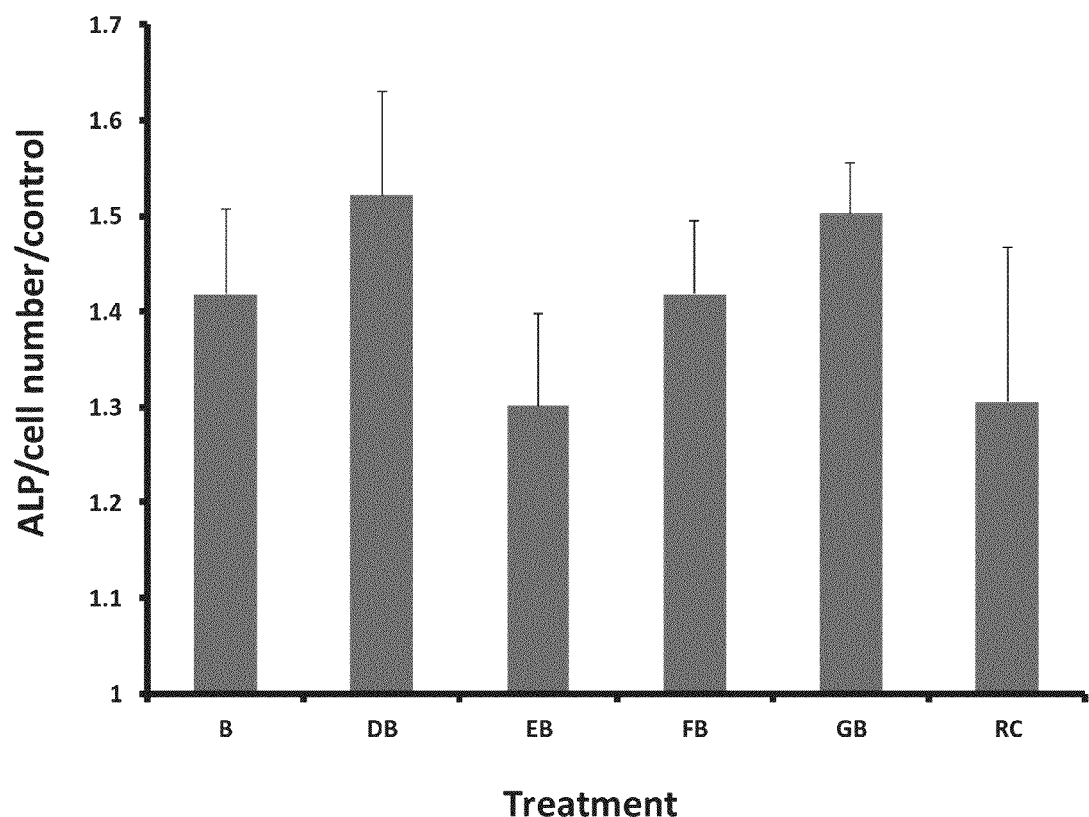

FIG. 6 shows the effects of Red clover isoflavone mixtures on osteoblast differentiation of MC3T3 cells. The total concentration of isoflavone in each treatment is 10 μM. For pair treatment, the ratio is 1:9. B is Biochanin A; DB is 1 μM of daidzein and 9 μM of Biochanin A; EB is 1 μM of equol and 9 μM of Biochanin A; FB is 1 μM of Formononetin and 9 μM of Biochanin A; GB is 1 μM of genistein and 9 μM of Biochanin A; and RC is Red clover extract. ALP/cell number ratio obtained in each treatment is normalized by the control to quantify relative osteoblast activities.

Figure 7:
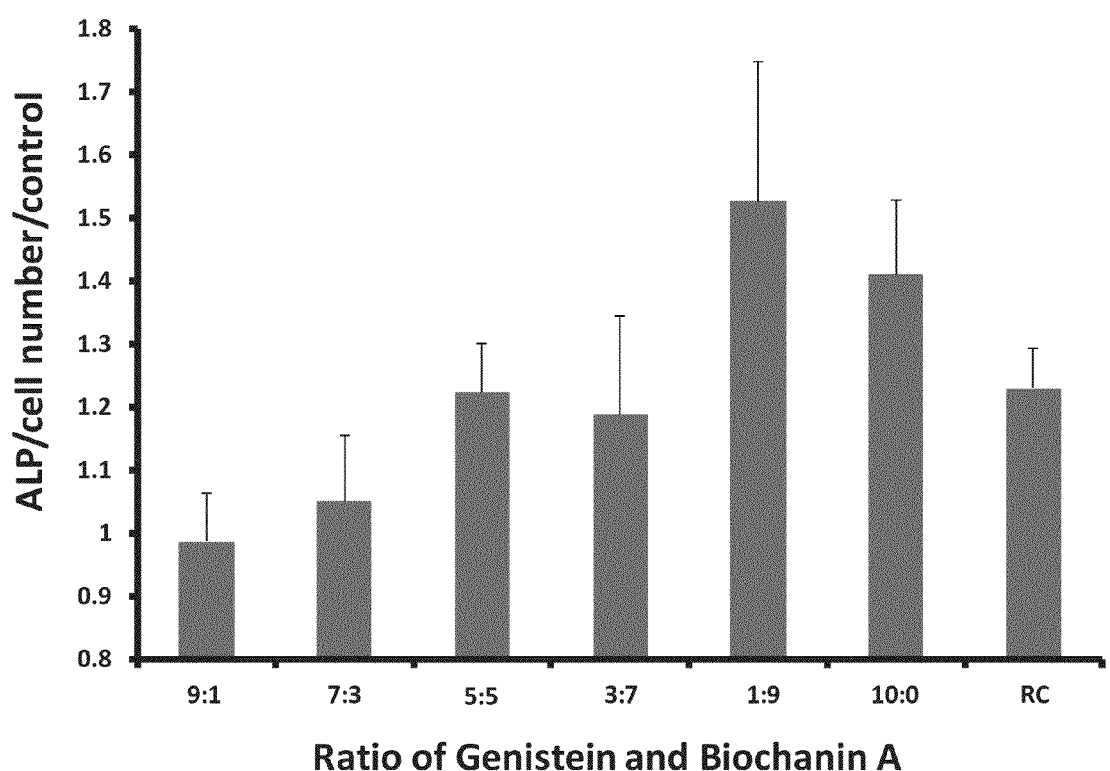

FIG. 7 shows the effects of progressive increase of genistein in a mixture of genistein and Biochanin A on the osteoblast differentiation of MC3T3 cells. The total concentration of isoflavone in each treatment is 10 μM. Effect of Red clover extract is also tested. ALP/cell number ratio obtained in each treatment is normalized by the control to quantify relative osteoblast activities.

Figure 8:
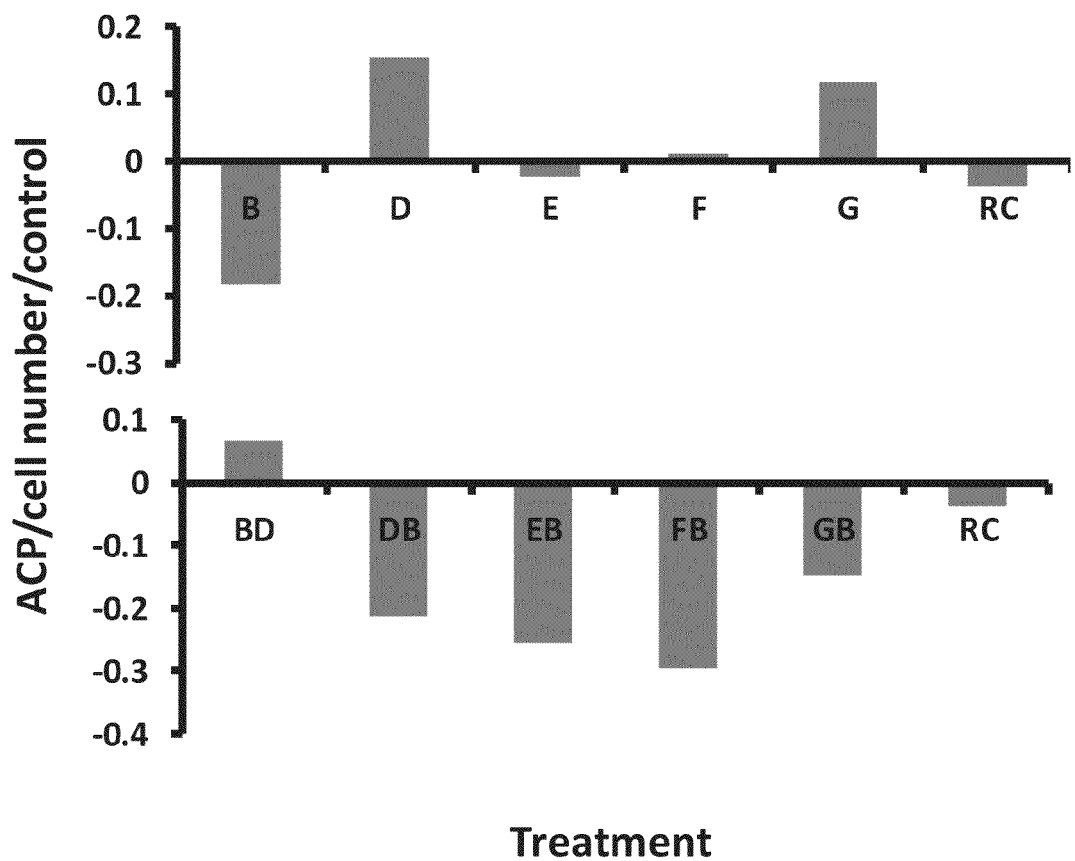

FIG. 8 shows the inhibition of osteoclast differentiation by Red clover isoflavones. The total concentration of isoflavone in each treatment is 10 μM. B: Biochanin A; D: daidzein; E: equol; F: formononetin; G: genistein; and RC: Red clover extract. For pair treatment, the ratio is 1:9. BD is 1 μM of Biochanin A and 9 μM of daidzein; DB is 1 μM of daidzein and 9 μM of Biochanin A; EB is 1 μM of equol and 9 μM of Biochanin A; FB is 1 μM of Formononetin and 9 μM of Biochanin A; GB is 1 μM of genistein and 9 μM of Biochanin A; and RC is Red clover extract. ACP/cell number ratio obtained in each treatment is normalized by the control to quantify relative osteoclast activities.

Figure 9:
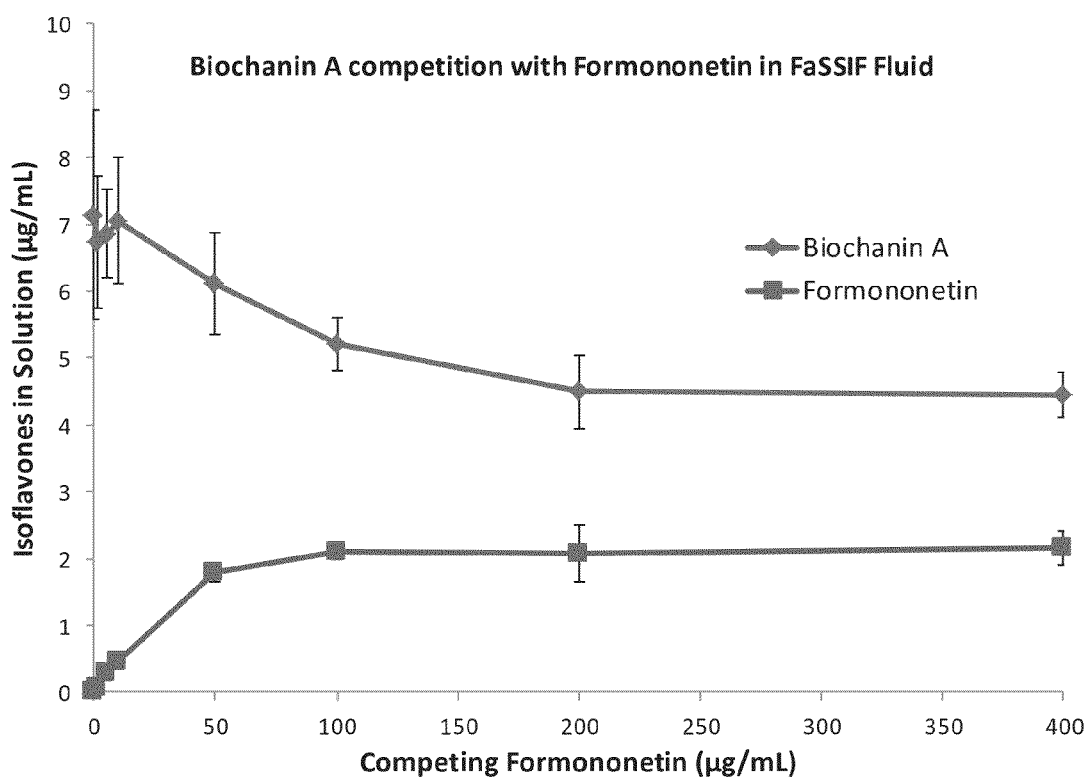

FIG. 9 shows the effects of Formononetin on the solubility of Biochanin A in fasted simulated intestinal fluid (FaSSIF). The amount of Biochanin A in the mixture is 200 μg/mL.

Figure 10:
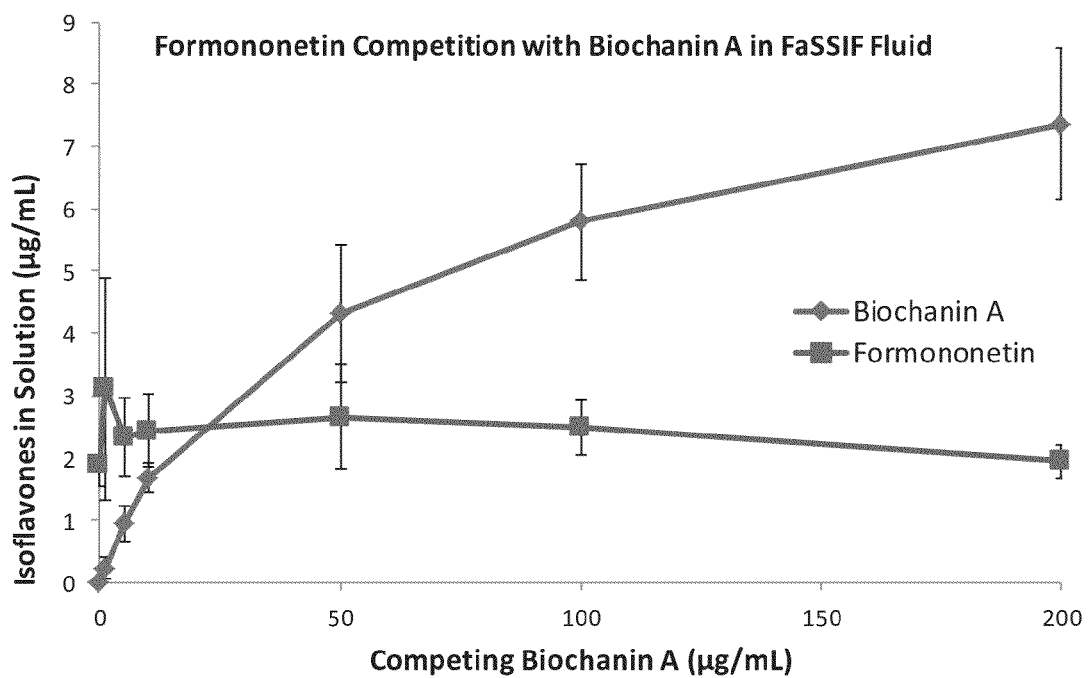

FIG. 10 shows the effects of Biochanin A on the solubility of Formononetin in fasted simulated intestinal fluid (FaSSIF). The amount of Formononetin in the mixture is 50 μg/mL.

Figure 11:
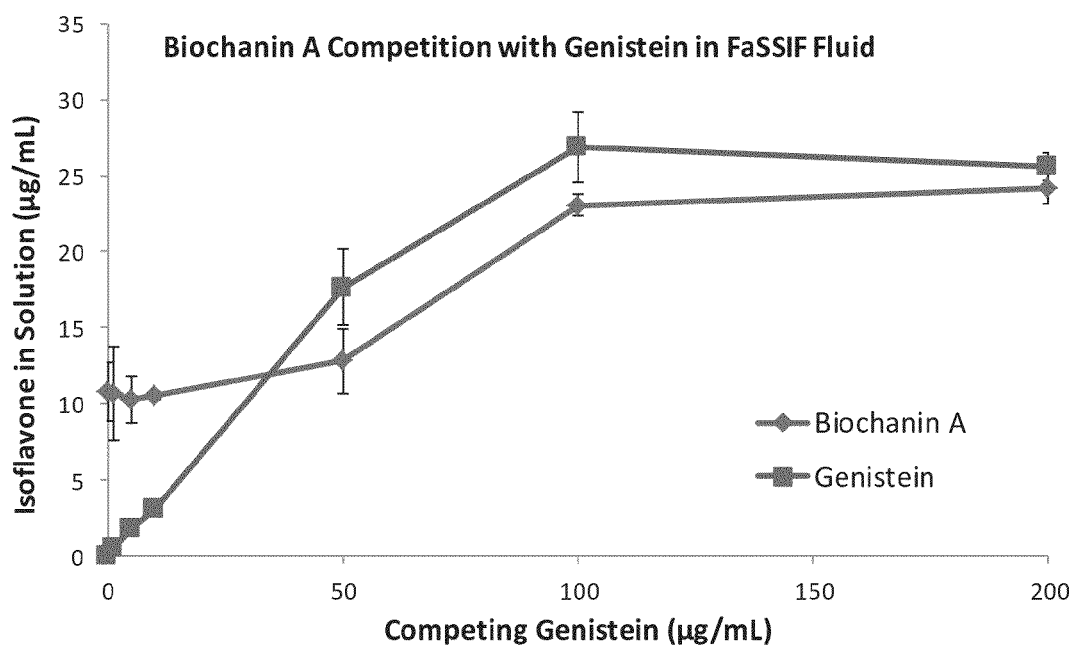

FIG. 11 shows the effects of genistein on the solubility of Biochanin A in fasted simulated intestinal fluid (FaSSIF). The amount of Biochanin A in the mixture is 200 μg/mL.

Figure 12:
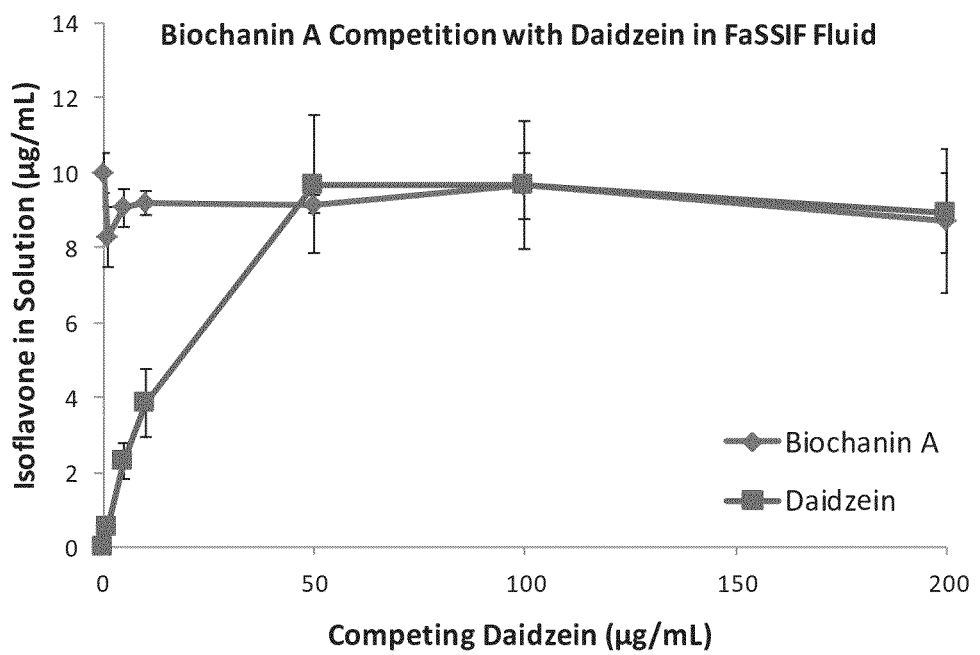

FIG. 12 shows the effects of daidzein on the solubility of Biochanin A in fasted simulated intestinal fluid (FaSSIF). The amount of Biochanin A in the mixture is 200 μg/mL.

Figure 13:
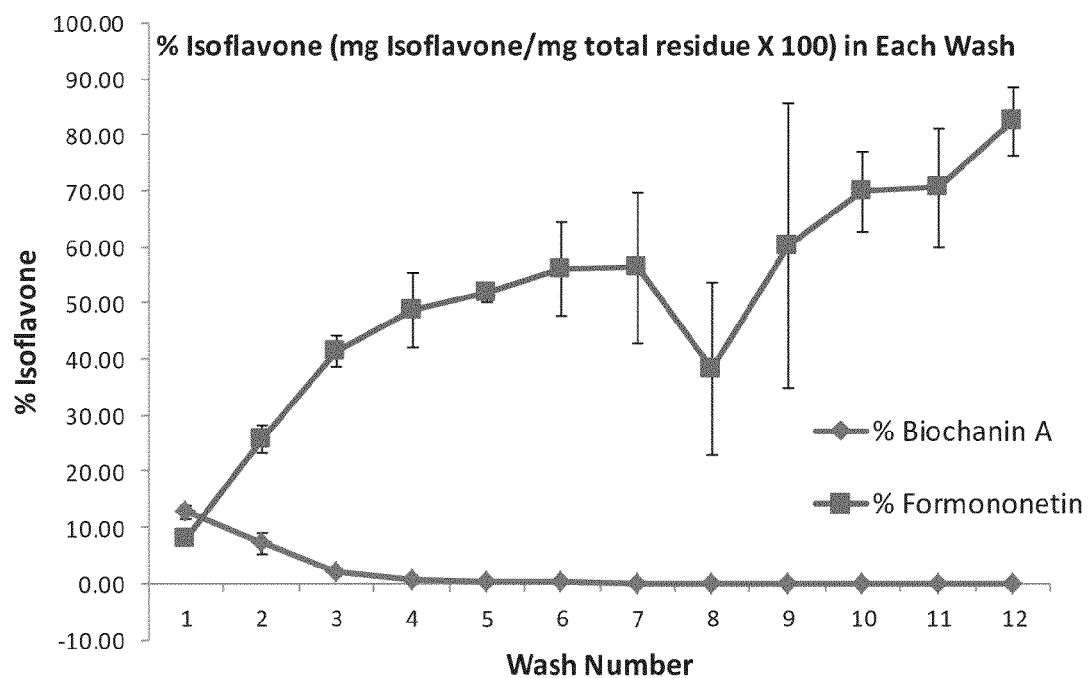

FIG. 13 shows the Isoflavone profiles of a commercial Red clover extract (Shaanxi, 40% total phytoestrogen) after sequential extraction with methanol.

Figure 14:
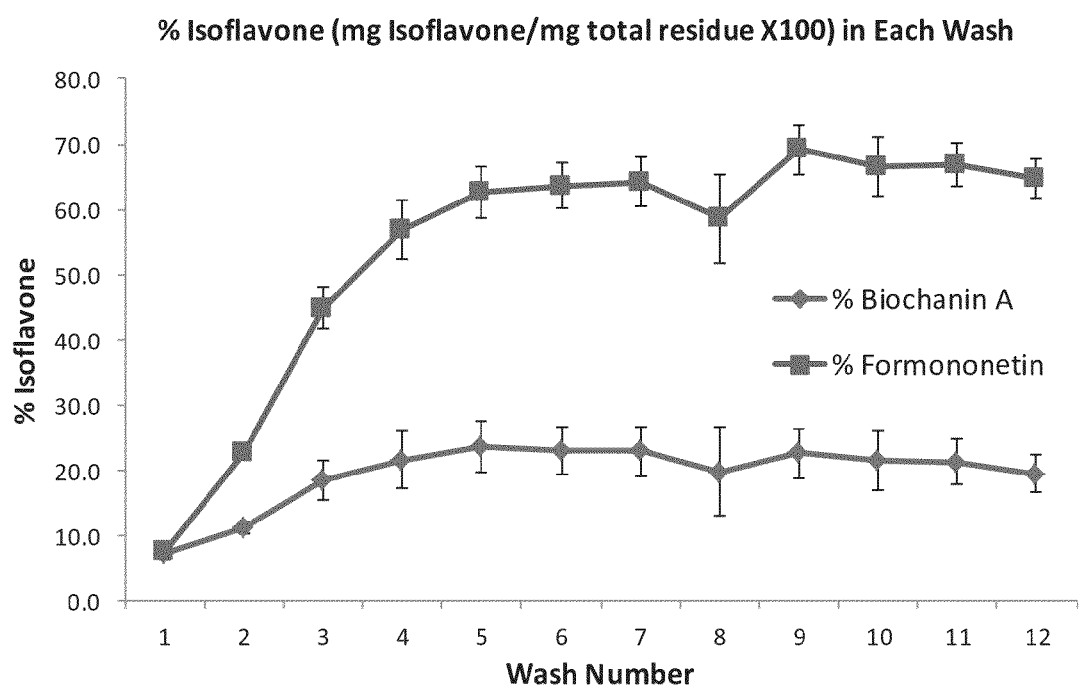

FIG. 14 shows the Isoflavone profiles of a commercial Red clover extract (Acetar, 40% total phytoestrogen) after sequential extraction with methanol.

Figure 15:
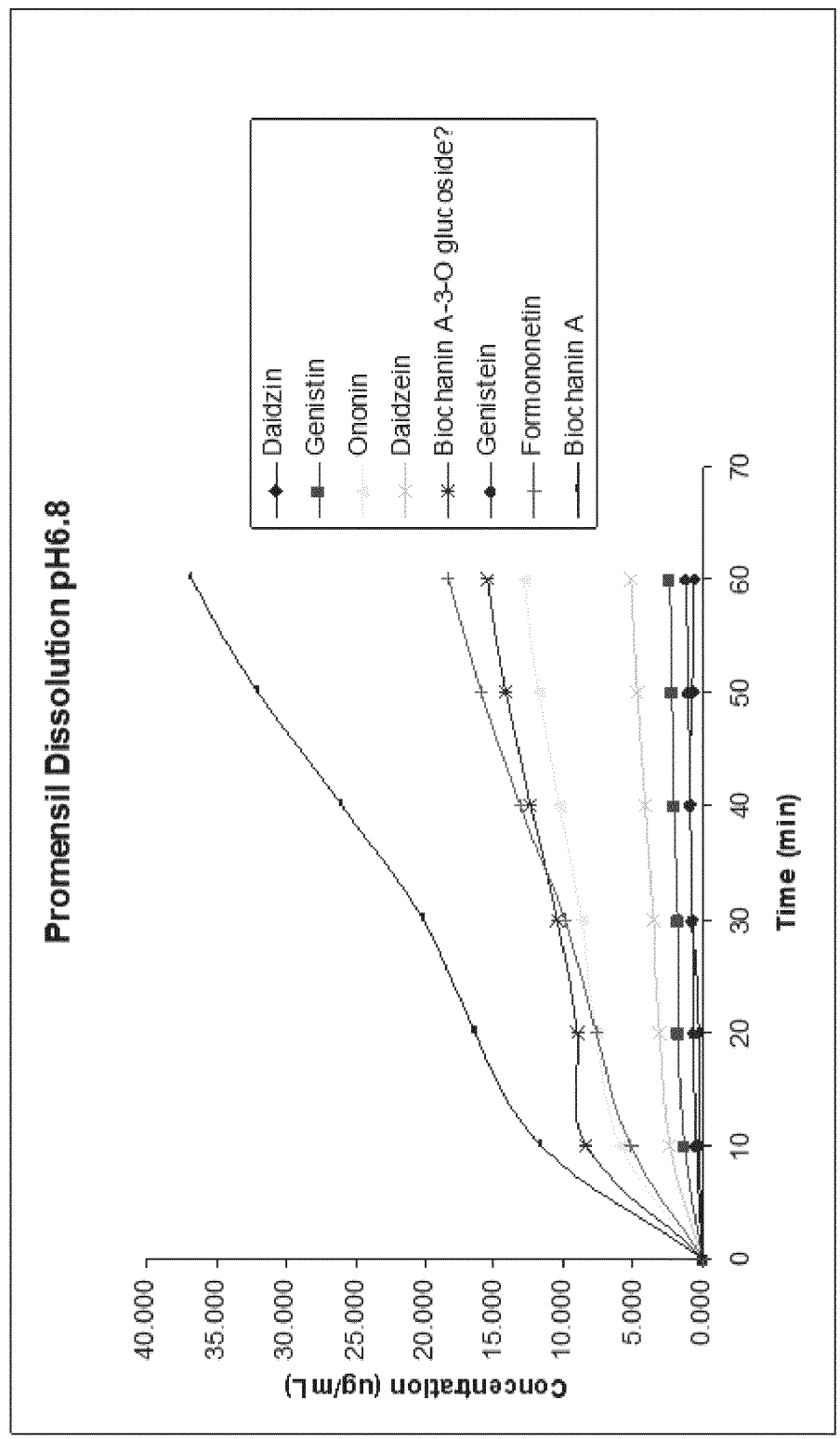

FIG. 15 shows a dissolution profile of two PROMENSIL tablets, each contains 40 mg of total phytoestrogens. The content of Biochanin A and Formononetin was not completely released.

DETAILED DESCRIPTION OF THE INVENTION

Biochanin A and Formononetin are the major components in Red clover. Their colonic metabolites, genistein and daidzein are also present in minute quantities (Beck, Rohr et al. 2005). A colonic metabolite of daidzein, equol, has been shown to have the highest estrogenicity among the red clover phytoestrogens (Magee 2011).

As shown below, the two major aglycones of Red clover, Biochanin A and Formononetin are highly insoluble in the gastrointestinal fluids. Daidzein and genistein, two minute components in Red clover, are also insoluble, although they are more soluble than Biochanin A and formononetin.

In the present invention, Biochanin A, formononetin, daidzein and genistein are found interacting with each other at the solubility level. The presence of one phytoestrogen may enhance or inhibit the solubility of the other phytoestrogen.

Lack of solubility, high first-pass gut and liver metabolism and colonic bacteria metabolism are responsible for the highly variable and extremely low bioavailability of the active components.

In one embodiment, the present invention provides a composition comprising active ingredients in Red clover, which are optimized to reduce the rate of bone loss in postmenopausal women by modulating bone remodeling. In one embodiment, the composition comprises at least 80% of Biochanin A, and no more than 20% of genistein. In another embodiment, the composition comprises at least 80% of Biochanin A, and at least 2% of genistein. In another embodiment, the ratio of Biochanin A and genistein ranges from 8:1 to 20:1.

In one embodiment, the composition contains at least 80% of Biochanin A, no more than 8% of genistein, and no more than 6% each of formononetin and daidzein. In one embodiment, the composition contains at least 80% of Biochanin A, at least 5% of genistein, and no more than 6% each of formononetin and daidzein. In one embodiment, the ratio of Biochanin A and Formononetin ranges from 20:1 to 10:1. In another embodiment, the ratio of Biochanin A and daidzein ranges from 20:1 to 10:1.

In one embodiment, the composition comprises a dosage of total isoflavones ranging from 1 to 10 mg.

In one embodiment, the compositions disclosed herein are obtained through synthetic processes, synthetic sources or natural sources.

In one embodiment, the present invention provides dosage forms of the compositions that will minimize first-pass metabolism, enhance exposure to active ingredients and minimize inter-individual variability.

In one embodiment, the composition is formulated as parenteral, buccal, sublingual, and other non-oral dosage forms including, but not limited to, topical, subcutaneous, intramuscular and intravenous dosage forms.

In one embodiment, the composition is formulated in the form of tablets, granules, injection, powder, solution, suspension, or capsules.

In one embodiment, the present invention also provides methods of using the compositions disclosed herein for modulating bone remodeling, comprising the step of administering the composition to a subject in need thereof. In one embodiment, the composition is formulated as parenteral, buccal, sublingual, or other non-oral dosage forms including, but not limited to, topical, subcutaneous, intramuscular and intravenous dosage forms.

In one embodiment, the present invention also provides methods of using the compositions disclosed herein for treating or preventing osteoporosis, comprising the step of administering the composition to a subject in need thereof. In one embodiment, the composition is formulated as parenteral, buccal, sublingual, or other non-oral dosage forms including, but not limited to, topical, subcutaneous, intramuscular and intravenous dosage forms.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

The objective of this study is to track the events that occur in the lumen of the gastrointestinal tract. The goals are to identify the stability of Red clover components, their physical and enzymatic stability, solubility and absorbability.

Twenty-five red clover extracts containing a diverse composition of Biochanin A, Formononetin, Genistein, Daidzein and their glucosides, along with other minute quantities of coumestrols and lignans have been prepared either using solvent extraction or a variety of cultivars. In one embodiment, the aerial portion of red clovers, leaves, stems or leaves and stems, were dried powdered. The plant material was extracted with 50% ethanol at 50° C. for 1 hour. The resultant sample was centrifuged and the ethanolic component was removed and dried.

Figure 1:
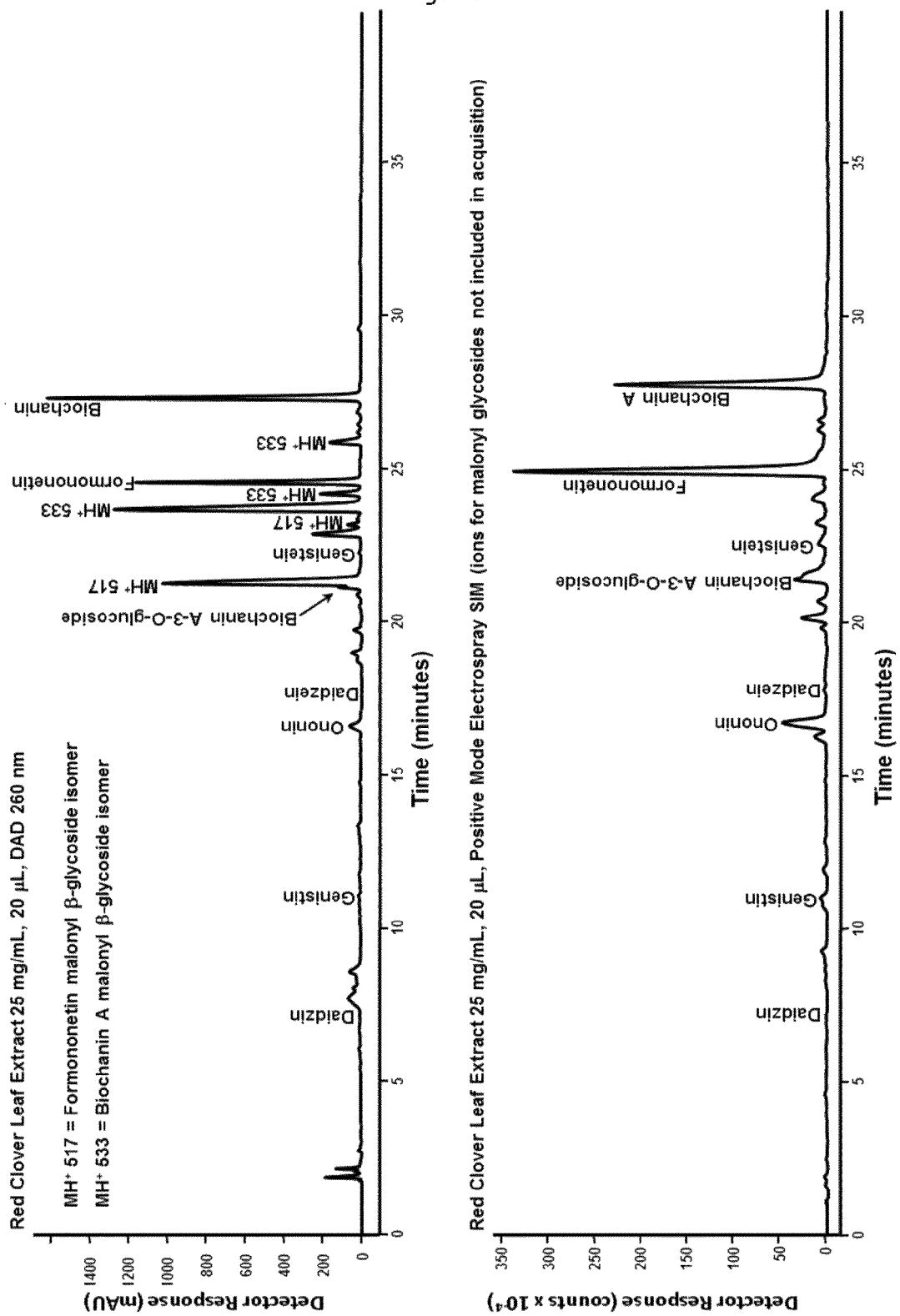
FIG. 1 shows a typical LC/MS chromatogram showing the composition of a Red clover extract.

A chromatographic analysis showed that the major ingredients in these extracts are the glucosides of Formononetin and Biochanin A and their respective aglycones (FIG. 1). Tiny amounts of genistein, daidzein and their glycosides were also found. These data are consistent with what is reported in the literature (Krenn, Unterrieder et al. 2002).

A study of the stability of the key components of a Red clover extract in artificial gastric and intestinal juice showed that the glucosides were partially (<25%) converted to their respective aglycones.

According to the literature, Formononetin and Biochanin A are de-methylated by the intestinal micro flora to produce two active metabolites daidzein and genistein, respectively (Hur and Rafii 2000). However, the importance of this metabolic pathway at this site is questioned (Tolleson, Doerge et al. 2002). To understand the relative importance of fecal metabolism, the metabolic rate of red clover phytoestrogens was measured.

Fresh human fecal samples were collected from 4 volunteers. Five grams of each were pooled together and mixed well with 30 mL BHI culture medium. The fecal suspension was centrifuged at 200 g for 5 min and supernatant was decanted and centrifuged at 5,000 g for another 30 min. The resultant precipitate was re-suspended with 10 mL BHI medium to produce intestinal micro flora solution.

As the biotransformation of drugs by human intestinal bacteria was determined in a 5 mL incubation system containing 250 µL, intestinal microflora solution, 50 µL, stock solution in DMSO in BHI medium. The incubation system was anaerobically incubated at 37° C. in a GasPak™ EZ Anaerobe Pouch System for 0 h, h, 72 h, and 120 h for red clover isoflavones (the final concentrations for Biochanin A, daidzein, equol, Formononetin, and genistein were 100 µM each). Zero-minute incubations served as controls. Reactions were stopped by extracting samples with ml of ethanol twice. The two ethanol extractions were combined, dried and re-suspended in 80% methanol for HPLC/MS analysis.

Figure 2:
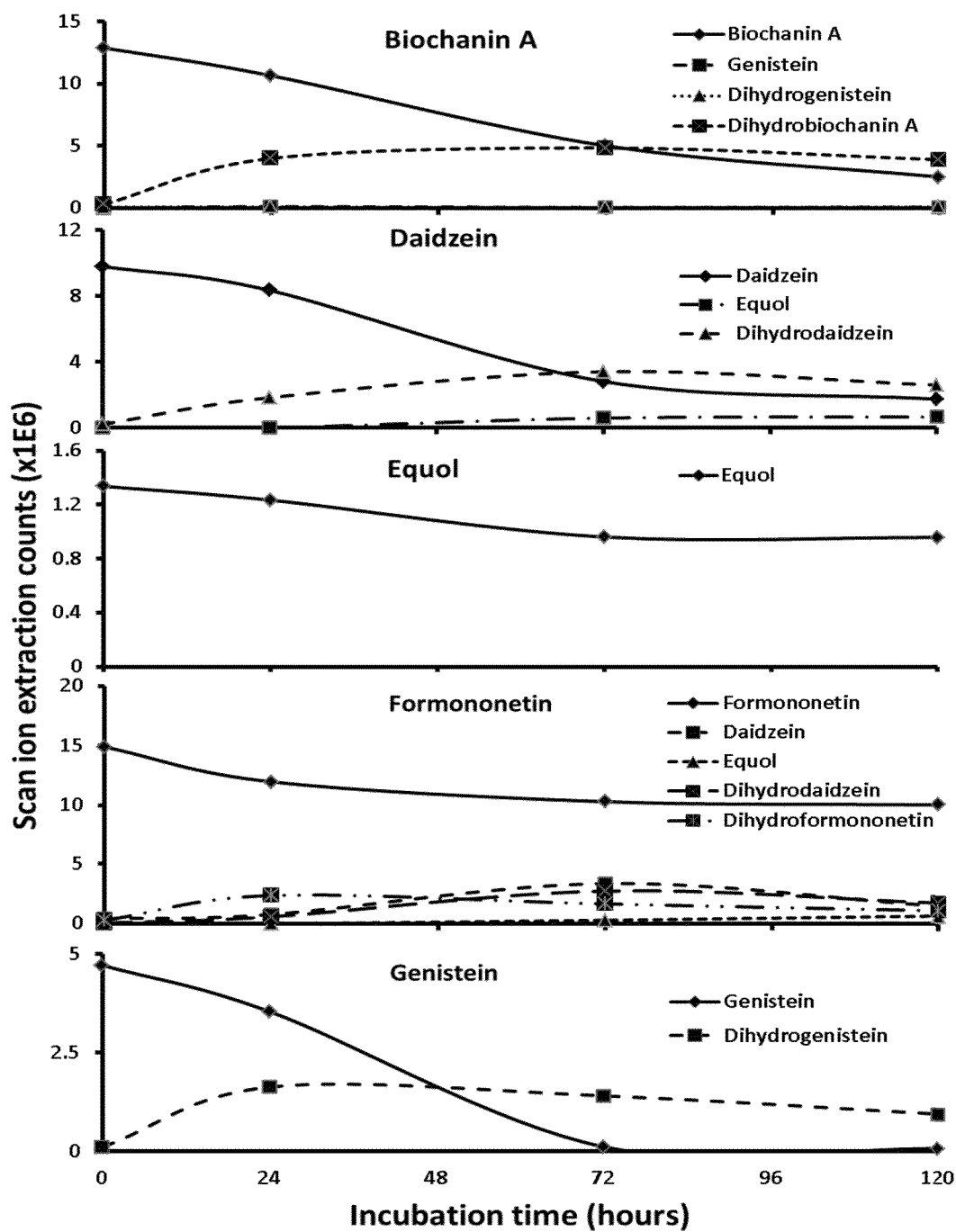
FIG. 2 shows the metabolism of the isoflavone mixtures by human fecal bacteria.

Red clover isoflavones are shown to be metabolized extensively by human intestinal microflora (FIG. 2). When Biochanin A was incubated with intestinal microflora, dihydrobiochanin A, genistein, and dihydrogenistein were formed. Daidzein was metabolized into dihydrodaidzein, and equol. Equol was the most resistant to bio-transformation. At the end of 120 hours, there was still over 60% of equol left in the incubation media, while there were less than 5% of Biochanin A, daidzein, and genistein left. The bio-transformed products of equol were not identified in this study. Formononetin was biotransformed into dihydroformononetin, dihydrodaidzein, daidzein, and equol. At the end of 120-hour incubation, there was over 20% of Formononetin remained. Genistein was bio-transformed into dihydrogenistein.

This set of studies clearly showed that extensive Phase I metabolism occurs in the lower part of the intestinal lumen.

Red clover extracts were subjected to permeability measurements using Caco-2 and MDCK cells. Permeability across these barriers provides an indication of absorbability.

The permeability values of Formononetin, Biochanin A, daidzein and genistein are quite high, suggesting that these components are highly absorbable (Table 1). Equol has also been shown to be absorbable. However, the glucosides of the aglycones such as Biochanin A glucoside and ononin have poor permeability suggesting the bioavailability of the sugar conjugates are poorly absorbed. These results are consistent with that reported in the literature in that when these glycosides are administered to either animals or humans, no glycosides could be detected in the blood stream (Setchell, Brown et al. 2002).

TABLE 1

CaCo-2 permeability of isoflavone in a Red clover extract

| Isoflavones | Mean Peff, cm/sec | STDEV |
|---|---|---|
| Biochanin A glucoside | 1.64E−08 | 1.11E−09 |
| Biochanin A | 1.08E−05 | 3.83E−07 |
| Daidzein | 2.66E−05 | 1.11E−06 |
| Daidzin | 5.36E−07 | 8.30E−08 |
| Formononetin | 2.20E−05 | 6.85E−07 |
| Genistein | 2.75E−05 | 1.22E−06 |
| Genistin | 3.46E−07 | 9.20E−08 |
| Ononin | 1.22E−07 | 1.93E−08 |

The results from the permeability study show that it would be beneficial to convert all the glucosides to their respective aglycones. Two advantages of adopting this strategy: a. the variability in the rate and extent of conversion from glucosides to aglycones between subjects will be removed. A more consistent pattern of aglycone absorption is anticipated. b. dosage calculation for the bioactives will be reduced to the aglycones only. This simplifies the standardization process.

An optimal extract of Red clover should consist of the aglycones only. An enzymatic or chemical conversion of the glucosides to their respective aglycones prior to extraction will be desirable. This can be accomplished using the literature methods (Tsao, Papadopoulos et al. 2006).

Example 2

The objectives of this example are to evaluate gut and liver metabolism of Biochanin A, Formononetin, daidzein, genistein and equol. Parameters obtained from these studies are used for estimating the pharmacokinetics of these five components.

Human liver microsomes, intestinal microsomes, and hepatocytes of human female origin were purchased from XenoTech. All chemicals were purchased from Sigma-Aldrich. Isoflavones (biochanin A, daidzein, equol, Formononetin, and genistein) were first dissolved in DMSO and then mixed according to a randomized table, consisting of 60 samples. The final DMSO in buffer or media was kept at 0.1%. Protocols supplied by XenoTech Inc., the supplier, were used for glucuronidation with microsomal incubation, and hepatocyte incubation. Samples were analyzed using LC/MS.

Figure 3:
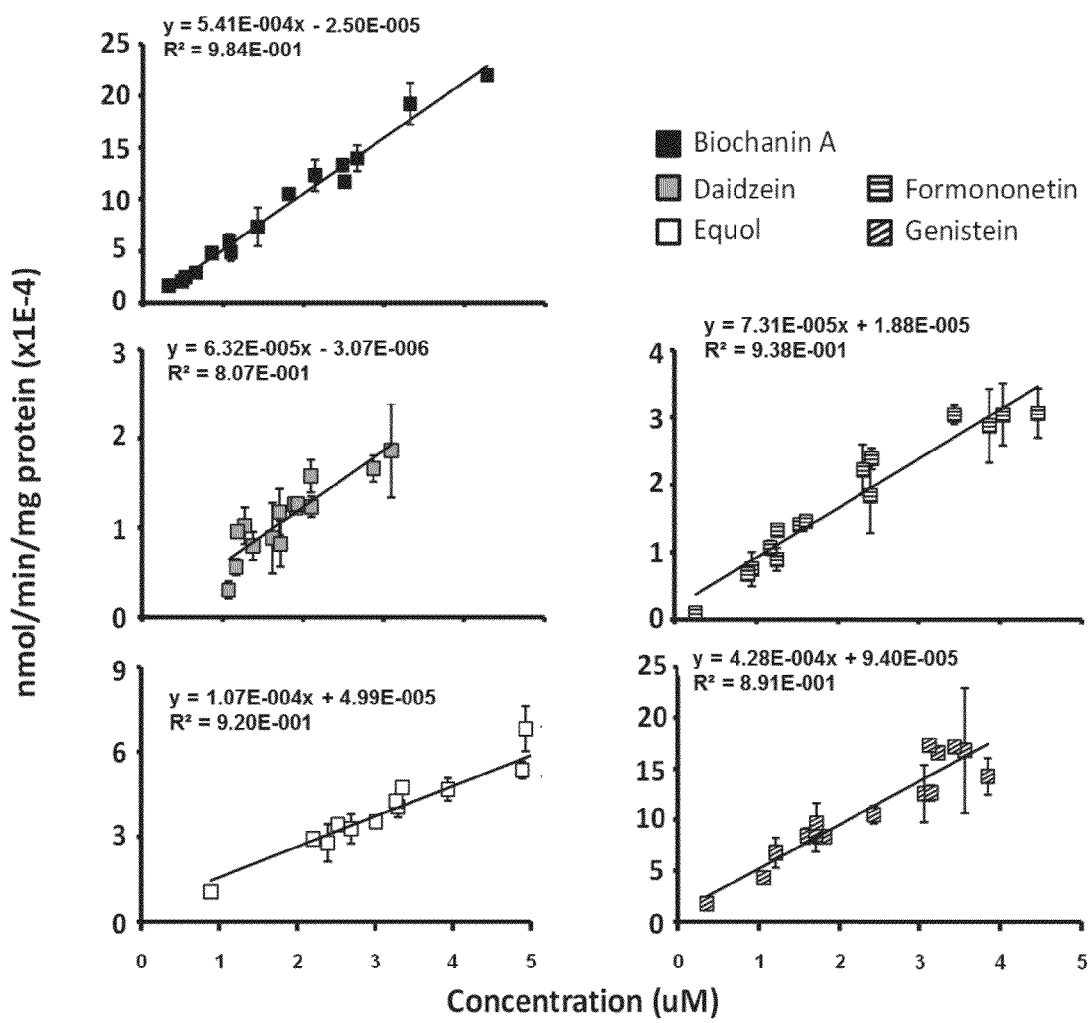
FIG. 3 shows the metabolism of the isoflavone mixtures by human intestinal microsomes.

FIG. 3 shows that metabolism of the mixtures by human intestinal microsomes: Biochanin A (5.41E-4 ml/min/mg protein)>genistein (4.28E-4 ml/min/mg protein)>equol (1.07E-ml/min/mg protein)>daidzein (6.32E-5 ml/min/mg protein)>Formononetin (7.31E-5 ml/min/mg protein).

Figure 4:
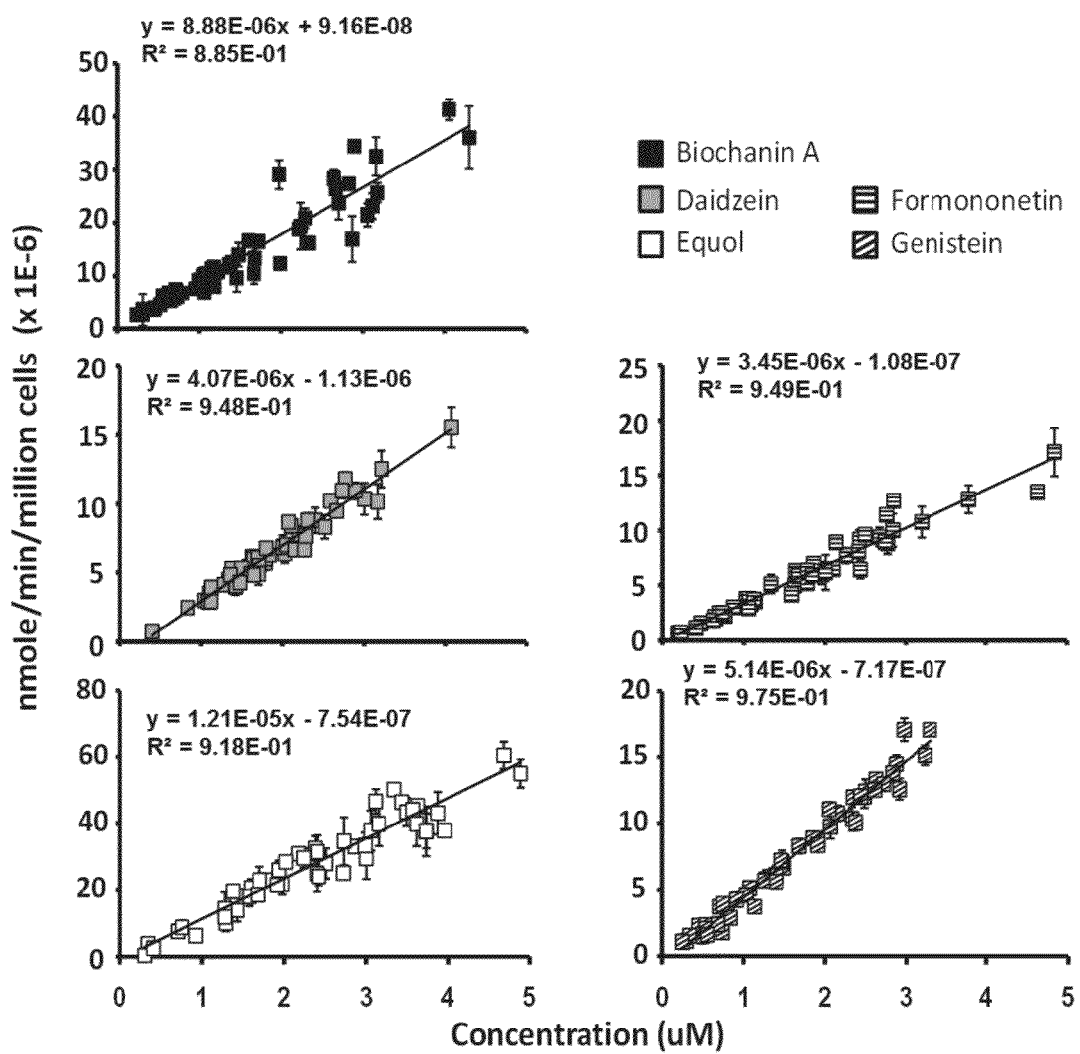
FIG. 4 shows the metabolism of the isoflavone mixtures by human hepatocytes.

FIG. 4 shows the rate of metabolism of the mixtures by human hepatocytes. The rates are: equol (1.21E-5 ml/min/million cells)>biochanin A (8.88E-6 ml/min/million cells)>genistein (5.14E-6 ml/min/million cells)>daidzein (4.07E-6 ml/min/million cells)>Formononetin (3.45E-6 ml/min/million cells).

From these studies, it is clearly shown that there are no metabolic interactions between the five components. In these metabolic studies, no Phase I metabolites were detected suggesting that the formation of Phase I metabolites, such as daidzein and genistein are formed in the intestinal lumen (Example 1). This piece of information is important in that the rate of formation of these metabolites is dependent on the solubility of Formononetin and Biochanin A. These results are consistent with that reported by Howes et al (2002) in that the peak time of the Phase I metabolites is delayed.

Example 3

The objectives of this study are to evaluate the effects of individual isoflavones of Red clover and their combinations on osteoblast and osteoclast differentiation.

Materials and Methods

Effects of isoflavones on the differentiation of osteoblast in MC3T3 cells and differentiation of osteoclast in Raw264.7 cells were determined as described in Ge et al., 2006 and followed Garcia Palacios et al., 2005. Cell numbers were measured with CellTag from Li-Cor Biosciences. Both activities of alkaline and acid phosphatase were measured with a plate reader at 405 nm.

Isoflavones were first dissolved in DMSO and stock solutions were prepared at 10 mM and the final concentration of total isoflavones in test solution was 10 µM.

Osteoblast and osteoclast differentiations were quantified by measuring activities of alkaline phosphatase (ALP) and acidic phosphatase (ACP). ALP is highly expressed by the mature osteoblasts and ACP is expressed by osteoclasts. Values of integrated intensity of fluorescence from Celltag staining serve as a correction factor for the difference in cell numbers. Therefore, ALP/cell number and ACP/cell number ratios are used to quantify osteoblast and osteoclast activities.

Results

Osteoblast Differentiation

Confluence MC3T3 cells were treated with 10 µM of isoflavones for 1 week and then the activity of alkaline phosphatase (ALP) was measured as an indicator of differentiation. Although the difference among isoflavone treatments was not significant, cells treated with Biochanin A consistently showed the highest ALP activity (FIG. 5). To examine if there were any synergistic effects, two isoflavones were mixed in a 1:9 ratio and tested in the final concentration of 10 µM. Mixtures with higher ratios (90%) of biochanin A were usually more effective in enhancing the osteoblast differentiation of MC3T3 cells than individual isoflavones alone or their combinations. In the example shown here cells treated with daidzein:Biochanin A (1:9) and genistein:Biochanin A (1:9) had higher ALP activities than Biochanin A alone (FIG. 6). To examine the effect of genisterin:Biochanin ratio on osteoblast differentiation, genistein was mixed with an increased concentration of Biochanin A (an increment of 10%). With the increased concentration of Biochanin A, the differentiation enhancing ability of the mixture increased and then dropped off when the mixture only contained Biochanin A (FIG. 7).

Osteoclast Differentiation

Raw246.7 cells were treated with MCSF and RANKL to stimulate the differentiation of osteoclasts. Isoflavones were added at the final concentration of 10 µM to examine their ability to inhibit differentiation. Cells treated with Biochanin A and its mixtures showed the highest inhibition in osteoclast differentiation (FIG. 8).

Conclusions

Contrary to its low estrogenicity (Beck, Unterrieder et al. 2003), Biochanin A is found to be most effective in enhancing the differentiation of osteoblast and to inhibit the differentiation of osteoclasts. Mixtures of Red clover aglycones containing high proportions of Biochanin A show synergistic effects. In one embodiment, the preferred ratios of the components at the site of action are 80 to 90% of Biochanin A, up to 20% genistein, and no more than 10% each of daidzein and Formononetin.

Example 4

The objectives of this study are: 1. To evaluate solubility interactions among the four phytoestrogens, which are native to Red clover, namely, Biochanin A, Formononetin, daidzein and genistein; 2. To evaluate potential differences in physicochemical properties of extracts containing the same amounts of phytoestrogens.

Materials and Methods

Interactions Among Isoflavones

Isoflavones: daidzein, genistein, Formononetin and Biochanin A were obtained from Indofine. Simulated intestinal fluid buffer powder mimicking a fasted state (FaSSIF) was obtained from Biorelevant SIF media, Biorelevant.com, Switzerland.

To prepare accurate concentrations of isoflavones in microtubes, stock solutions of individual isoflavones were prepared at 1 mg/mL in methanol. The amount of isoflavone designated to be held constant was provided at a concentration that well exceeded (about 20×) the saturation concentration for that isoflavone. The appropriate amount of stock was transferred to each microtube and the material was dried down in a vacuum centrifuge.

In the case of Biochanin A competition with other flavones (daidzein, genistein and formononetin), the amount of Biochanin A was held constant at 200 µg in 1 ml buffer (saturation concentration for Biochanin A in FaSSIF is about 8 µg/mL). The competing isoflavone was prepared at 0, 1, 5, 10, 50, 100, 200 µg/mL (FIGS. 11 and 12) and, in the case of Formononetin, 400 µg/mL (FIG. 9).

In the case of Formononetin competition with Biochanin A, the amount of Formononetin was held constant at 50 µg in 1 ml buffer (saturation concentration for formononetin in FaSSIF is about 2 µg/mL). The competing Biochanin A was prepared at 0, 1, 5, 10, 50, 100 and 200 µg/mL (FIG. 10).

Each tube was then reconstituted with 1 mL of FaSSIF buffer, sonicated and allowed to equilibrate with occasional agitation for 24 hours at 37° C. This produced a solution that contained saturated isoflavone concentrations mimicking mammalian intestinal conditions.

At the end of 24 hours each tube containing isoflavones and FaSSIF buffer was briefly centrifuged at 5000 rpm in a microcentrifuge held at 37° C. (2 minutes). A portion of the supernatant (400 µL) was then immediately placed in a centrifugal filter unit (UltraFree-MC-GV 0.22 µM) and the sample filtered by centrifugation (8000 rpm, 5 minutes, 37° C.). Upon filtration 200 µL filtrate was immediately placed in a microtube and 200 µL, methanol added to ensure that the isoflavones remained in solution. The sample was mixed and 200 µL, of the mixture was transferred to injection vials provided with 200 µL, polypropylene injection inserts.

The samples were analyzed by HPLC with diode array detection at 260 nm using 20 µL, injections.

Results

When Biochanin A was placed in media representing fasted digestive juice at a concentration of 200 µg/mL at 37° C. (an amount about 25 times the soluble saturation value), the amount in solution was determined to be about 7.1 µg/mL (FIG. 9). As Formononetin was introduced, Biochanin A saturation concentration dropped in a dose dependent manner and was reduced to about 4.5 µg/mL in the presence of 400 µg/mL formononetin (FIG. 9).

When the experiment was done holding formononetin at 50 µg/mL (about 25 times Formononetin's saturation solubility in fasted media), increasing concentrations of Biochanin A did not affect the saturation concentration of Formononetin (FIG. 10). It is concluded that the presence of Biochanin A does not influence the saturation concentration of the much less soluble Formononetin.

In experiments where Biochanin A solubility was investigated in the presence of varying concentrations of genistein, a different set of results was obtained. When Biochanin A was placed in media representing fasted digestive juice at a concentration of 200 µg/mL at 37° C. the amount in solution was determined to be about 10.8 µg/mL (FIG. 11). As genistein was introduced, Biochanin A saturation concentration increased in a dose dependent manner and reached about 24.2 µg/mL in the presence of 200 µg/mL genistein (FIG. 11). It is concluded that the solubility of Biochanin A is enhanced by the presence of genistein in fasted digestive medium.

In experiments where Biochanin A saturation solubility was investigated in the presence of varying concentrations of daidzein, a set of results different from both the Formononetin and genistein experiments were obtained. When Biochanin A was placed in media representing fasted digestive juice at a concentration of 200 µg/mL at 37° C. the amount in solution was determined to be about 10.0 µg/mL (FIG. 12). As daidzein was introduced, the Biochanin A saturation concentration remained unaffected and was about 8.7 µg/mL in the presence of 200 µg/mL daidzein (FIG. 12). It is concluded that the solubility of biochanin A is unaffected by the presence of daidzein in fasted digestive media.

This set of studies clearly showed that interactions among isoflavones are not predictable. The solubility of Biochanin A in simulated intestine juice is reduced by Formononetin, enhanced by genistein, and not affected by daidzein.

Similar results are obtained when simulated intestinal juice mimicking the fed state was used (data not shown).

Solubility of Isoflavones in Red Clover Extracts

Two Red clover extracts containing 40% total isoflavones were examined: Shaanix Tianzun BN 078201205123 and Acetar TYR081023.

One gram extract was placed in a disposable 12 mL glass screw top test tube. 10 mL of 100% methanol was added and the tube was capped. The tube was mixed and placed in an ultrasonic water bath for 5 minutes. The tube was then shaken every 15 minutes for 1 hour. Mixing was done at room temperature. At the end of the 1 hour incubation the tube was centrifuged (Eppendorf 5804 R, 1500 rpm, 10 minutes) and the supernatant was collected and set aside. Another 10 mL of methanol was introduced to the tube on top of the sediment and the material was sonicated, mixed and incubated as described above. This process was repeated such that 12 washes from the material were collected. The precipitate from the final wash was re-suspended in methanol.

A 100 µL aliquot collected from each 10 mL wash was diluted 1:10 with 80% methanol, centrifuged and the supernatant analyzed by HPLC with diode array detection at 260 nm using 5 or 20 µL injections. 20 µL injections were used for later washes (wash 6-12) in which daidzein, genistein and Biochanin A concentrations were much lowered.

The remaining wash supernatants as well as the re-suspended final residue were individually dried down in pre-weighed microtubes to provide an estimate of solid weight recovered in each wash.

An estimate of isoflavone concentrations in the original extracts was made by dissolving the extracts at 1 mg/mL in 80% methanol with warming and sonication. An aliquot was diluted 1:10 with 80% methanol and centrifuged. A 5 µL injection was analyzed by HPLC.

The two 40% isoflavone products extract (Acetar and Shaanxi) are found to be different from each other. There was a difference in appearance between the two 40% extracts as one has a color of dark green-gray (Acetar) and the other one is off white (Shaanxi) after extraction with methanol.

The Acetar extract did not release isoflavones as rapidly when compared to that of Shaanix (Comparing FIGS. 13 and 14). Biochanin A was still being extracted after 12 sequential extracts. It appears that something in the Acetar extract is binding the isoflavones and only slowly releasing them into the methanol (FIG. 14).

The results of this study clearly showed that isoflavones from different Red clover extracts produced using different procedures could have vastly different solubility. Since absorption of isoflavones is highly dependent on their solubility, isoflavones prepared from sources or materials with identical labels may have different bioavailability. This may in part explain the inconsistent clinical results reported in the literature (Booth, Piersen et al. 2006).

The hypothesis that solubility may be an issue of phytoestrogen absorption was tested by examining the dissolution profile of a commercially available Red clover product, PROMENSIL® (30 tablets in a box, Lot # [B] 48449, Exp. 03/2011).

FIG. 15 shows that the dissolution of phytoestrogens in the product is not complete, lending evidence to support the idea that an inappropriately formulated product will perform erratically because of absorption issues. It should also be pointed out that the phytoestrogens in PROMENSIL® consist of both aglycones and their glucosides. Compounding the bioavailability issue, both of these species are not completely dissolved under the experimental condition studied.

Example 5

The protocol used by (Moon, Sagawa et al. 2006) was used for measuring plasma protein binding of the absorbable aglycones. Parameters have been used for PBPK simulation. Conjugates of Biochanin A, Formononetin, Genistein, Daidzein and Equol are predominant components in plasma. The respective aglycones constitute less than 5% of the total concentration. Plasma protein binding of biochanin A, Formononetin, genistein and equol are over 97% and daidzein was approximately 80%.

Example 6

The objective of this example is to employ the proprietary pharmacodynamic/pharmacokinetic (PBPK) model to simulate the pharmacokinetic behavior of the active phytoestrogens in Red clover.

Results from Examples 1, 2 and 4 are used as inputs into the proprietary PBPK model to simulate plasma concentration profiles of the four phytoestrogens: Biochanin A, Formononetin, daidzein and genistein and their Phase II metabolites.

Using the parameters generated in Examples 1, 2 and 4, the proprietary PBPK model was adapted to describe the pharmacokinetics of Red clover isoflavones. The model was considered validated when the simulated results of Area Under the Curve (AUC) values of the Phase II metabolites are agreeable (within 2-fold, Table 2) with that published by Howes et al. (2002). Plasma levels of Phase II metabolites of the four isoflavones as reported by Howes et al. (2002) and as simulated using the proprietary PBPK model is compared in Table 2 (second and third columns, Table 2). The two sets of values are found to be agreeable, indicating the simulated results obtained are valid.

TABLE 2

Comparison of plasma levels of isoflavones obtained from clinical samples and simulation results using the PBPK model

| | $AUC_{0-24}$, ng*h/mL | | | |
|---|---|---|---|---|
| | Phase II metabolites | | Aglycone (simulation) | |
| | Howes' data* | Simulation | Oral | IV |
| Formononetin | 112 ± 35 | 123 | 9.47 | 1989 |
| Biochanin A | 518 ± 518 | 519 | 4.99 | 2422 |
| Daidzein | 891 ± 135 | 693 | 7.49 | 261 |
| Genistein | 1463 ± 115 | 1231 | 3.85 | 229 |

*Data reported by Howes et al (2002). Two Promensil tablets containing 32 mg of Formononetin, 49 mg of Biochanin A, 3 mg of daidzein and 3 mg of genistein were administered to subject per day.

The PBPK model was then used to simulate the AUC values of isoflavones after oral and intravenous administration. Plasma levels of aglycone of the four isoflavones after oral and intravenous administration (IV) of identical dose of isoflavones as that of Promensil are simulated using the PBPK model (fourth and fifth columns, Table 2). Comparing the AUC values obtained, it is observed that the AUC values of aglycone obtained after intravenous administration is approximately 20 to 500 times higher than those after oral administration.

This simulation suggests that bioavailability of phytoestrogens would be enhanced by administering the compounds via non-oral route such as intravenous route.

Howes et al's (2002) data also showed that AUC values among subjects are highly variable (>10 fold). This variation can be explained by the instability of glucosides, low solubility of the aglycones, interaction among aglycones at the solubility level, aglycone metabolism of the aglycones by colonic bacteria and high first-pass gut and liver metabolism. The end result is low bioavailability (0.2 to 3%).

High variability, low bioavailability and solubility limited absorption are the major causes for therapeutic failure. In a recent review (Lagari and Levis 2014), it was reported that there was a much higher proportion of clinical trials showing Red clover phytoestrogens were ineffective in treating postmenopausal bone loss and climacteric symptoms than the effective ones. Dosages used for clinical trials went as high as 80 mg total phytoestrogens.

Based on the results described in this invention, failure of Red clover therapy is not surprising because low solubility, high first-pass effects and variable colonic metabolism are key factors which lead to low bioavailability and high interindividual variability of the phytoestrogens.

Limited solubility of phytoestrogens in the small intestine may be responsible for the lack of a dose-dependent increase in clinical response to Red clover isoflavones (Booth, Piersen et al. 2006).

Commercially, it is common to find Red clover extracts containing higher proportions of Formononetin. As demonstrated in the present invention, Biochanin A is found to be the most effective and Formononetin is shown to lower Biochanin A's solubility in simulated intestinal fluid. Thus Red clover extracts containing high Formononetin are ineffective.

In the realm of solubility limitations, an effective combination of Red clover phytoestrogens should contain very low levels of Formononetin (<2 to 10%).

Genistein has been found to have dual functions. It enhances the solubility of Biochanin A and acts synergistically with Biochanin A in enhancing bone remodeling.

A low percentage of daidzein and Formononetin has also been found to have synergistic antiresorptive effects.

Taking together, an ideal combination of Red clover phytoestrogens should contain a high content of Biochanin A (>80%) and smaller contents of genistein, daidzein and Formononetin.

To avoid extensive first-pass effects, solubility issues and variable colonic metabolism, an alternative route of administration other than oral should be employed. Dosage forms for parenteral, topical, subcutaneous, intramuscular, intravenous, buccal or sublingual administration should be employed.

In one embodiment, the dosage of phytoestrogens can be less than 5-10% of the normal clinical dose, which is 80 mg. These low dosages should provide significantly higher plasma levels of Biochanin A, genistein, daidzein and Formononetin when compared to a regular 80 mg dose of Red clover isoflavones.

Assuming an 80 mg dose is marginally active (Lagari and Levis 2014), the combination of phytoestrogens as disclosed herein would greatly enhance clinical effectiveness of Red clover phytoestrogens.

REFERENCES

Beck, V., U. Rohr and A. Jungbauer (2005). "Phytoestrogens derived from red clover: an alternative to estrogen replacement therapy?" *J Steroid Biochem Mol Biol* 94(5): 499-518.

Beck, V., E. Unterrieder, L. Krenn, W. Kubelka and A. Jungbauer (2003). "Comparison of hormonal activity (estrogen, androgen and progestin) of standardized plant extracts for large scale use in hormone replacement therapy." *J Steroid Biochem Mol Biol* 84(2-3): 259-268.

Booth, N. L., C. R. Overk, P. Yao, J. E. Burdette, D. Nikolic, S. N. Chen, J. L. Bolton, R. B. van Breemen, G. F. Pauli and N. R. Farnsworth (2006). "The chemical and biologic profile of a red clover (*Trifolium pratense* L.) phase II clinical extract." *J Altern Complement Med* 12(2): 133-139.

Booth, N. L., C. E. Piersen, S. Banuvar, S. E. Geller, L. P. Shulman and N. R. Farnsworth (2006). "Clinical studies of red clover (*Trifolium pratense*) dietary supplements in menopause: a literature review." *Menopause* 13(2): 251-264.

Chen, J., H. Lin and M. Hu (2005). "Absorption and metabolism of genistein and its five isoflavone analogs in the human intestinal Caco-2 model." *Cancer Chemother Pharmacol* 55(2): 159-169.

Chen, J., S. Wang, X. Jia, S. Bajimaya, H. Lin, V. H. Tam and M. Hu (2005). "Disposition of flavonoids via recycling: comparison of intestinal versus hepatic disposition." *Drug Metab Dispos* 33(12): 1777-1784.

Fernandez, E., S. Gallus, C. Bosetti, S. Franceschi, E. Negri and C. La Vecchia (2003). "Hormone replacement therapy and cancer risk: a systematic analysis from a network of case-control studies." *Int J Cancer* 105(3): 408-412.

Gambacciani, M., M. Ciaponi and A. R. Genazzani (2007). "The HRT misuse and osteoporosis epidemic: a possible future scenario." *Climacteric* 10(4): 273-275.

Gambacciani, M., P. Monteleone, A. Sacco and A. R. Genazzani (2003). "Hormone replacement therapy and endometrial, ovarian and colorectal cancer." *Best Pract Res Clin Endocrinol Metab* 17(1): 139-147.

Howes, J., M. Waring, L. Huang and L. G. Howes (2002). "Long-term pharmacokinetics of an extract of isoflavones from red clover (*Trifolium pratense*)." *J Altern Complement Med* 8(2): 135-142.

Hur, H. and F. Rafii (2000). "Biotransformation of the isoflavonoids biochanin A, formononetin, and glycitein by *Eubacterium limosum*." *FEMS Microbiol Lett* 192(1): 21-25.

Jia, X., J. Chen, H. Lin and M. Hu (2004). "Disposition of flavonoids via enteric recycling: enzyme-transporter coupling affects metabolism of biochanin A and formononetin and excretion of their phase II conjugates." *J Pharmacol Exp Ther* 310(3): 1103-1113.

Krenn, L., I. Unterrieder and R. Ruprechter (2002). "Quantification of isoflavones in red clover by high-performance liquid chromatography." *J Chromatogr B Analyt Technol Biomed Life Sci* 777(1-2): 123-128.

Lagari, V. S. and S. Levis (2014). "Phytoestrogens for menopausal bone loss and climacteric symptoms." *J Steroid Biochem Mol Biol* 139: 294-301.

Liu, J., J. E. Burdette, H. Xu, C. Gu, R. B. van Breemen, K. P. Bhat, N. Booth, A. I. Constantinou, J. M. Pezzuto, H. H. Fong, N. R. Farnsworth and J. L. Bolton (2001). "Evaluation of estrogenic activity of plant extracts for the potential treatment of menopausal symptoms." *J Agric Food Chem* 49(5): 2472-2479.

Ma, D. F., L. Q. Qin, P. Y. Wang and R. Katoh (2008). "Soy isoflavone intake inhibits bone resorption and stimulates bone formation in menopausal women: meta-analysis of randomized controlled trials." *Eur J Clin Nutr* 62(2): 155-161.

Magee, P. J. (2011). "Is equol production beneficial to health?" *Proc Nutr Soc* 70(1): 10-18.

Moon, Y. J., K. Sagawa, K. Frederick, S. Zhang and M. E. Morris (2006). "Pharmacokinetics and bioavailability of the isoflavone biochanin A in rats." *Aaps J* 8(3): E433-442.

Overk, C. R., P. Yao, L. R. Chadwick, D. Nikolic, Y. Sun, M. A. Cuendet, Y. Deng, A. S. Hedayat, G. F. Pauli, N. R. Farnsworth, R. B. van Breemen and J. L. Bolton (2005). "Comparison of the in vitro estrogenic activities of compounds from hops (*Humulus lupulus*) and red clover (*Trifolium pratense*)." *J Agric Food Chem* 53(16): 6246-6253.

Seelig, M. S., B. M. Altura and B. T. Altura (2004). "Benefits and risks of sex hormone replacement in postmenopausal women." *J Am Coll Nutr* 23(5): 482S-496S.

Setchell, K. D., N. M. Brown, L. Zimmer-Nechemias, W. T. Brashear, B. E. Wolfe, A. S. Kirschner and J. E. Heubi (2002). "Evidence for lack of absorption of soy isoflavone glycosides in humans, supporting the crucial role of intestinal metabolism for bioavailability." *Am J Clin Nutr* 76(2): 447-453.

Setchell, K. D. and A. Cassidy (1999). "Dietary isoflavones: biological effects and relevance to human health." *J Nutr* 129(3): 758S-767S.

Tolleson, W. H., D. R. Doerge, M. I. Churchwell, M. M. Marques and D. W. Roberts (2002). "Metabolism of biochanin A and formononetin by human liver microsomes in vitro." *J Agric Food Chem* 50(17): 4783-4790.

Tsao, R., Y. Papadopoulos, R. Yang, J. C. Young and K. McRae (2006). "Isoflavone profiles of red clovers and their distribution in different parts harvested at different growing stages." *J. Agric. Food Chem.* 54: 5797-5805.

Wuttke, W., H. Jarry and D. Seidlova-Wuttke (2007). "Isoflavones—safe food additives or dangerous drugs?" *Ageing Res Rev* 6(2): 150-188.

What is claimed is:

1. An in vitro method of enhancing osteoblast differentiation, comprising the step of contacting osteoblasts with a composition comprising biochanin A and genistein, wherein the ratio of biochanin A to genistein is 9:1, and the composition comprises a dosage of total phytoestrogens ranging from 1 to 10 mg, wherein the concentration of biochanin A is 9 μM and the concentration of genistein is 1 μM.

2. The method of claim 1, wherein the composition comprises the dosage of total phytoestrogens no more than 10 mg.

3. The method of claim 1, wherein said composition inhibits osteoclast differentiation.

4. An in vitro method of inhibiting osteoclast differentiation, comprising the step of contacting osteoclasts with a composition comprising biochanin A and genistein, wherein the ratio of biochanin A to genistein is 9:1, and the composition comprises a dosage of total phytoestrogens ranging from 1 to 10 mg, wherein the concentration of biochanin A is 9 μM and the concentration of genistein is 1 μM.

5. The method of claim 4, wherein the composition comprises the dosage of total phytoestrogens no more than 10 mg.

6. The method of claim 4, wherein said composition enhances osteoblast differentiation.

7. A method of treating osteoporosis in a subject, comprising the step of administering to the subject in need thereof a composition comprising biochanin A and genistein, wherein the composition provides the subject biochanin A and genistein at a ratio of 9:1, and the composition is formulated as intravenous dosage forms, said composition comprises a dosage of total phytoestrogens ranging from 1 to 10 mg, wherein the concentration of biochanin A is 9 μM and the concentration of genistein is 1 μM.

8. The method of claim 7, wherein the composition is formulated in the form of injection, solution, or suspension.

9. The method of claim 7, wherein the composition comprises a dosage of total phytoestrogens less than 4 to 8 mg.

10. The method of claim 7, wherein the composition comprises the dosage total phytoestrogens no more than 10 mg.

* * * * *